US 6,610,269 B1

(12) United States Patent
Klaveness et al.

(10) Patent No.: US 6,610,269 B1
(45) Date of Patent: Aug. 26, 2003

(54) CONTRAST AGENTS

(75) Inventors: Jo Klaveness, Oslo (NO); Anne Naevestad, Oslo (NO); Helge Tolleshaug, Oslo (NO)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/422,977

(22) Filed: Oct. 22, 1999

Related U.S. Application Data

(63) Continuation of application No. PCT/GB98/01197, filed on Apr. 24, 1998.
(60) Provisional application No. 60/048,044, filed on May 30, 1997.

(30) Foreign Application Priority Data

Apr. 24, 1997 (GB) .............................................. 9708265

(51) Int. Cl.[7] .............................................. A61K 49/00
(52) U.S. Cl. ...................... 424/9.1; 424/1.11; 424/1.65; 424/1.69
(58) Field of Search ............................ 424/1.11, 1.65, 424/1.69, 9.1, 9.3, 9.5, 9.51; 128/9.52, 654, 653.2; 600/458, 441; 534/7, 10–16; 435/320.1; 530/300

(56) References Cited

U.S. PATENT DOCUMENTS 5,766,591 A * 6/1998 Brooks et al. ............ 424/184.1
6,051,207 A * 4/2000 Klaveness et al. ........... 424/9.1
6,113,878 A * 9/2000 Dean et al. ................ 424/1.69

FOREIGN PATENT DOCUMENTS

| DE | 195 22 774 A | | 1/1997 |
| GB | 2225579 | * | 6/1990 |
| WO | WO 96 23524 A | | 8/1996 |

OTHER PUBLICATIONS

Chemical Abstracts, 126:26, Jun. 30, 1997, abstract No. 340590, Nitschke, R. et al.; "A Modified Confocal Laser Scanning Microscope Allows Fast Ultraviolet Ratio Imaging of Intracellular Ca2+ activity using Fura–2", XP002074474.

Chemical Abstracts, 121;17, Oct. 24, 1994, abstract No. 199859, Condrau, Marc A. et al.; "Time–resolved Flow Cytometry for the Measurement of Instrument Design and Experimental Results", XP002074475.

* cited by examiner

Primary Examiner—Dameron L. Jones
(74) Attorney, Agent, or Firm—Bacon & Thomas

(57) ABSTRACT

The invention provides a composition of matter of the formula (I): V—L—R, where V is a vector moiety having affinity for an angiogenesis-related endothelias cell receptor, L is a linker moiety or a bond and R is a detectable moiety, characterized in that V is a non-peptidic organic group, or V is peptidic and R is a macromolecular or particulate species providing a multiplicity of labels detectable in in vivo imaging.

23 Claims, No Drawings

SEQUENCE LISTING

```
<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<221> NAME/KEY: UNSURE
<222> LOCATION: (10)..(10)
<223> OTHER INFORMATION: Xaa represents an unidentified amino acid
<221> NAME/KEY: SITE
<222> LOCATION: (1)..(16)
<223> OTHER INFORMATION: An HDGF peptide fragment

<400> SEQUENCE: 1

Leu Pro Ala Leu Pro Glu Asp Gly Gly Xaa Gly Ala Phe Pro Pro Gly
1               5                   10                  15

<210> SEQ ID NO 2
<211> LENGTH: 17
<212> TYPE: PRT
<213> ORGANISM: Artificial Sequence
<220> FEATURE:
<221> NAME/KEY: SITE
<222> LOCATION: (1)..(1)
<223> OTHER INFORMATION: Xaa represents Ala or Ser
<221> NAME/KEY: SITE
<222> LOCATION: (2)..(2)
<223> OTHER INFORMATION: Xaa represents Leu or Arg
<221> NAME/KEY: SITE
<222> LOCATION: (4)..(4)
<223> OTHER INFORMATION: Xaa represents Ala or Gly
<221> NAME/KEY: SITE
<222> LOCATION: (5)..(5)
<223> OTHER INFORMATION: Xaa represents Leu or Pro
<221> NAME/KEY: SITE
<222> LOCATION: (1)..(17)
<223> OTHER INFORMATION: An HDGF peptide fragment

<400> SEQUENCE: 2

Xaa Xaa Pro Xaa Xaa Ala Gly Thr Met Ala Ala Gly Ser Ile Thr Thr
1               5                   10                  15

Leu

<210> SEQ ID NO 3
<211> LENGTH: 54
<212> TYPE: PRT
<213> ORGANISM: Artificial Sequence
<220> FEATURE:
<221> NAME/KEY: SITE
<222> LOCATION: (1)..(54)
<223> OTHER INFORMATION: A modified platelet factor 4

<400> SEQUENCE: 3
```

```
-continued

Ser Gln Val Arg Pro Arg His Ile Thr Ser Leu Glu Val Ile Lys Ala
1               5                   10                  15

Gly Pro His Cys Pro Thr Ala Gln Leu Ile Ala Thr Leu Lys Asn Gly
                20                  25                  30

Arg Lys Ile Cys Leu Asp Leu Gln Ala Pro Leu Tyr Lys Lys Ile Ile
            35                  40                  45

Lys Lys Leu Leu Glu Ser
        50

<210> SEQ ID NO 4
<211> LENGTH: 53
<212> TYPE: PRT
<213> ORGANISM: Artificial Sequence
<220> FEATURE:
<221> NAME/KEY: SITE
<222> LOCATION: (1)..(53)
<223> OTHER INFORMATION: A modified platelet factor 4

<400> SEQUENCE: 4

Ser Gln Val Arg Pro Arg His Ile Thr Ser Leu Glu Val Ile Lys Ala
1               5                   10                  15

Gly Pro His Cys Pro Thr Ala Gln Leu Ile Ala Thr Leu Lys Asn Gly
                20                  25                  30

Arg Lys Ile Cys Leu Asp Leu Gln Ala Pro Leu Tyr Lys Ile Ile Lys
            35                  40                  45

Lys Leu Leu Glu Ser
        50

<210> SEQ ID NO 5
<211> LENGTH: 16
<212> TYPE: PRT
<213> ORGANISM: Artificial Sequence
<220> FEATURE:
<221> NAME/KEY: SITE
<222> LOCATION: (1)..(16)
<223> OTHER INFORMATION: Modified platelet factor 4

<400> SEQUENCE: 5

Glu Ala Glu Glu Asp Gly Asp Leu Gln Cys Leu Cys Val Lys Thr Thr
1               5                   10                  15
```

CONTRAST AGENTS

This application is a continuation of pending international application number PCT/GB98/01197 filed Apr. 24, 1998 (of which the entire disclosure of the pending, prior application is hereby incorporated by reference), which itself is a continuation-in-part of U.S. provisional application number 60/048,044 filed May 30, 1997.

This invention relates to diagnostic imaging techniques in which a disease state may be imaged using a targeted contrast agent and to targeted contrast agents suitable for use in such techniques. More particularly the invention relates to the use of such contrast agents in which the targeting vector binds to receptors associated with angiogenesis. Such contrast agents may thus be used for diagnosis of for example malignant diseases, heart diseases, inflammation-related diseases, rheumatoid arthritis and Kaposi's sarcoma. Moreover such agents may be used in therapeutic treatment of these diseases.

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes which break down the proteins of the basement membrane, as well as inhibitors which limit the action of these potentially harmful enzymes. The other prominent effect of angiogenic factors is to cause endothelial cells to migrate and divide. Endothelial cells which are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodeling of tissues, including wound healing and inflammatory processes. Tumors must initiate angiogenesis when they reach millimeter size in order to keep up their rate of growth. As angiogenesis is accompanied by characteristic changes in the endothelial cells and their environment, this process is a promising target for therapeutic intervention. Inhibition of angiogenesis is also considered to be a promising strategy for antitumor therapy. The transformations accompanying angiogenesis are also very promising for diagnosis, an obvious example being malignant disease, but the concept also shows great promise in inflammation and a variety of inflammation-related diseases, including atherosclerosis, the macrophages of early atherosclerotic lesions being potential sources of angiogenic factors. These factors are also involved in re-vascularisation of infarcted parts of the myocardium, which occurs if a stenosis is released within a short time.

Angiogenesis involves receptors which are unique to endothelial cells. The surface of these cells is remodelled in preparation for migration, and cryptic structures are exposed where the basement membrane is degraded, in addition to the variety of-proteins which are involved in effecting and controlling proteolysis. A number of known receptors/targets associated with angiogenesis are listed in Table 1 below. In the case of tumors, the resulting network of blood vessels is usually disorganised, with the formation of sharp kinks and also arteriovenous shunts. Using the targeting principles described in the present disclosure, angiogenesis may be detected by the majority of the imaging modalities in use in medicine.

TABLE 1

Receptors/targets associated with angiogenesis
Receptors/Targets $\alpha_2$-antiplasmin
basement membrane components
basic fibroblast growth factor (bFGF)
biglycan (dermatan sulfate proteoglycan)
cartilage-derived inhibitor [inhibitor]
CD34
collagen type I, IV, VI, VIII
decorin (dermatan sulfate proteoglycan)
dermatan sulfate proteoglycans
endoglin
endosialin
endothelin
epidermal growth factor (heparin-binding)
fibrin
fibrinopeptide B
fibroblast growth factor, FGF-3, basic
fibronectin
Flt-1/KDR, Flt-4 (VEGF receptor)
FLT-1 (fms-like tyrosine kinase) (VEGF-A receptor)
heparan sulfate
hepatocyte growth factor
hepatocyte growth factor receptor (c-met)
hyaluronan
insulin-like growth factor
insulin-like growth factor/mannose-6-phosphate receptor
integrins: $\beta_3$ and $\beta_5$, integrin $\alpha_v\beta_3$, integrin $\alpha_6\beta_1$ (laminin receptor), integrin $\alpha_6$, integrin $\beta_1$, integrin $\alpha_2\beta_1$, integrin $\alpha_5$ (subunit of the fibronectin receptor), integrin $\alpha_v\beta_5$, fibrin receptors
interferon-$\alpha$, $\beta$ [inhibitors]
interleukins: IL-8, IL-12 [inhibitor]
Jagged gene product.
laminin
laminin fragments
leukemia inhibitory factor
Ly-6 (a lymphocyte activation protein)
matrix metalloprotease-2
metalloproteinases
metalloproteinase inhibitors
MHC class II
Notch gene product
placental growth factor
placental proliferin-related protein
plasminogen
plasminogen activator
plasminogen activator inhibitor-1
plasminogen activator receptor
platelet-derived growth factor (e.g. type BB)
platelet-derived endothelial cell growth factor
platelet factor 4 [inhibitor]
pleiotropin
proliferin, proliferin-related protein
receptor tyrosine kinases
selectins: E-selectin
SPARC
stress proteins (molecular charperones) (glucose regulated, heat shock families)
syndecan
tissue inhibitor of metalloproteinases (e.g. TIMP-2)
thrombin
thrombin-receptor-activating tetradecapeptide
thrombospondin [inhibitor]
TIE receptors (tyrosine kinases with Ig- and EGF-like domains)
tissue factor
transforming growth factor-$\alpha$, $\beta$
tumor growth factor-$\alpha$
tumor necrosis factor
urokinase-type plasminogen activator receptor
Vascular endothelial growth factor-A
Vascular endothelial growth factor-related protein

TABLE 1-continued

Receptors/targets associated with angiogenesis

Receptors/Targets

Vascular endothelial growth factor-A receptor
vitronectin
von Willebrand factor note: many hormones, growth factors and other compounds which bind to cell surface receptors may act as vectors by binding to their receptors, or, when they are already bound to the cell surface, they are targets for vectors that bind to them, for instance antibodies.

As indicated above, many undesired conditions are associated with neovascularization or angiogenesis, the development or proliferation of new blood vessels. Examples of such conditions are listed in Table 2 below

TABLE 2

Diseases and indications associated with angiogenesis

Diseases/Indications arteriovenous malformations
astrocytomas
atherosclerosis
breast cancers
choriocarcinomas
colorectal cancers
gingivitis
glioblastomas
gliomas
hemangiomas (childhood, capillary)
hepatomas
hyperplastic endometrium
inflammation (e.g. chronic)
ischemic myocardium
Kaposi sarcoma
lung cancers
macular degeneration
melanoma
metastasis
neuroblastomas
occluding peripheral artery disease
osteoarthritis
ovarian cancers
pancreatic cancers
prostate cancers
psoriasis
retinopathy (diabetic, proliferative)
rheumatoid arthritis
scleroderma
seminomas
skin cancers
solid tumor formation
ulcerative colitis The surface cells, endothelial cells, of such new blood vessels have greater than normal concentrations of various surface or transmembrane receptors, such as for example receptor tyrosine kinases (RTK), and it has been proposed to use radiolabelled or chromophore-labelled antibodies to such receptors, or similarly labelled analogues of natural protein ligands for such receptors, as a means of detecting centres of angiogenesis (see for example WO95/26364 (Orion), WO96/30046 (Genentech) and WO95/12414 (Repligen)).

Peptidic ligands however have relatively few attachment sites for detectable labels (reporters) and attachment of reporters at many sites on such peptidic ligands will affect the conformations which the ligand may adopt. A further problem with peptides is that they are often unstable in vivo.

There is therefore still a need for effective targeted contrast agents with affinities for receptors associated with angiogenesis.

The present invention addresses this need in two ways—firstly by providing targeted contrast agents based on non-peptidic ligands (vectors)—and secondly by providing targeted contrast agents based on macromolecular or particulate reporters providing a multiplicity of detectable labels (multireporters).

Thus viewed from one aspect the invention provides a composition of matter of formula I $$V—L—R \qquad (I)$$

wherein V is a vector moiety having affinity for an angiogenesis-related endothelial cell receptor, L is a linker moiety or a bond, and R is a detectable reporter moiety, preferably a gas-free detectable reporter moiety, e.g. detectable in an imaging procedure, such as in vivo imaging of the human or vascularized non-human animal body (e.g. mammalian, avian or reptilian body), characterised in that V is a non-peptidic organic group, or V is peptidic and R is a macromolecular or particulate species providing a multiplicity of labels detectable in in vivo imaging.

Where R is a macromolecular or particulate species providing a multiplicity of labels, these may be labels which individually are detctable (e.g. paramagnetic or radioactive species) or they may interact to produce a detectable material, e.g. by virtue of a cooperative magnetic phenomenon. Examples of such multi-reporters include polychelates and polyionic species, and ferromagnetic, ferrimagnetic and superparamagnetic particles.

In many instances, the composition of matter of formula I will be a characterisable compound. In others it may be a combination of compounds bonded or otherwise associated, eg. conjugated, with each other. For convenience sake, the composition of matter will be referred to hereinafter as an agent.

By "gas" is meant a material or mixture of materials which is gaseous at 37° C. By "gas-free" is meant a reporter which does not contain sufficient gas to be detectable in ultrasonography in vivo. Contrast agents comprising gas-containing reporters are described in our copending International Patent Application No. PCT/GB97/02958 filed Oct. 28, 1997.

Viewed from a further aspect the invention provides a pharmaceutical composition comprising an effective amount (eg. an amount effective to enhance image contrast in in vivo imaging) of an agent of formula I together with at least one pharmaceutically effective carrier or excipient.

Viewed from a still further aspect the invention provides the use of an agent of formula I for the manufacture of a contrast medium for use in a method of diagnosis involving administration of said contrast medium to an animate subject and generation of an image of at least part of said subject.

Viewed from a still further aspect the invention provides a method of generating an image of an animate human or non-human (preferably mammalian or avian) animal subject involving administering a contrast agent to said subject, eg. into the vascular system or the gi tract, and generating an image of at least a part of said subject to which said contrast agent has distributed, eg. by X-ray, MR, ultrasound, scintigraphy, PET, SPECT, electrical impedance, light or magnetometric imaging modalities, characterised in that as said contrast agent is used an agent of formula I.

Viewed from a further aspect the invention provides a method of monitoring the effect of treatment of a human or non-human animal subject with a drug to combat a condition associated with angiogenesis, e.g. a cytotoxic agent, said method involving administering to said subject an agent of formula I and detecting the uptake of said agent by endothelial cell receptors, in particular receptors in a region of angiogenesis, said administration and detection optionally but preferably being effected repeatedly, eg. before, during and after treatment with said drug.

Viewed from a yet further aspect the invention provides a process for the preparation of an agent of formula I, said process comprising conjugating (i) compound having binding affinity for an endothelial cell receptor associated with angiogenesis to (ii) a compound detectable in a diagnostic imaging procedure or a chelant compound and if necessary metallating chelant groups in the resultant conjugate with a metal ion detectable in a diagnostic imaging procedure.

The agents of formula I have three characteristic components: a vector (V); a linker (L); and a reporter (R). The vector must have the ability to target the compound to a region of angiogenesis, the reporter must be detectable in an in vivo diagnostic imaging procedure; and the linker must couple vector to reporter, at least until the reporter has been delivered to the region of angiogenesis and preferably until the imaging procedure has been completed.

Vectors

As the vector may be used any peptidic or, more preferably, non-peptidic compound having affinity for receptors associated with angiogenesis.

Non-peptidic compounds are preferably used as peptidic vectors will generally have poor biological stability and may provoke undesired responses by the body.

Preferably the vector is a compound which does not elicit any unacceptable biological response, especially one which does not actually promote angiogenesis.

Particularly preferably the vector is an angiogenesis inhibitor, especially preferably a non-peptidic angiogenesis inhibitor.

Examples of non-peptidic angiogenesis inhibitors are described in WO94/17084 (British Biotech), EP-A-618208 (Daiichi), WO94/13277 (ICRT), WO95/06473 (Nippon Kayaku), WO94/21612 (Otsuka), WO97/37655 (Merck), WO97/30035 (Zeneca), EP-A-678296 (Tsumura), WO94/18967 (Harvard), WO95/08327 (Dept. of Health and Human Services) (see also U.S. Pat. No. 4,590,201 (Merck)) and EP-A-652000 (Eli Lilly).

Examples of peptidic angiogenesis inhibitors are described in WO94/02446 (British Biotech), WO94/02447 (British Biotech), WO94/21625 (British Biotech), WO94/24140 (British Biotech), WO95/04033 (Celltech), EP-A-589719 (Eli Lilly), U.S. Pat. No. 5,399,667 (Frazier), EP-A-241830 (The General Hospital Corporation) and WO97/38009 (Merck).

Particular angiogenesis inhibitors under development include those listed in Table 3 below:

TABLE 3

| Angiogenesis Inhibitors | | | |
|---|---|---|---|
| Compound | Target indications | Company | Comments |
| Tecogalan sodium | Kaposi's sarcoma Solid tumors | Daiichi | sulfated polysaccharide peptidoglycan complex |
| AGM-1470 | Kaposi's sarcoma Malignant tumors | Takeda/Abbott | Fumagillin analog |
| CM101 | Cancer Metastasis | Carbomed | Polysaccharide exotoxin |
| Mitoflaxone GM-1603 | Solid tumors | Lipha Glycomed | Modified heparin |
| rPF4 | Kaposi's sarcoma Colon cancer Glioma Renal cell carcinoma Malignant melanoma | Replistatin Repligen | Recombinant human platelet factor-4 |
| MPF-4 | | Lilly | Modified human platelet factor-4 |
| Recombinant angiostatin Endostatin | | EntreMed | collagen fragment |
| Thalidomide | Brain, breast and prostate cancer | EntreMed | |
| DC101 | | ImClone Systems | Monoclonal antibody |
| OLX-514 | Solid tumors Sepsis | Aronex | |
| Raloxifene hydrochloride | | Lilly | |
| Suramin sodium | Metastatic hormone-refractory prostate carcinoma | Parke-Davis | |
| IL-12 | Kidney cancer | Roche | |
| Marimastat | Pancreatic, lung and brain cancer | British Biotech | |
| CAI | Wide range of cancers | NCI | Ca channel blocker | as well as the following peptidic and non-peptidic drug compounds:

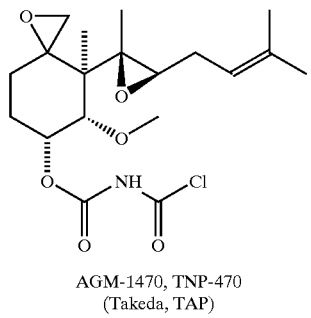

AGM-1470, TNP-470
(Takeda, TAP)

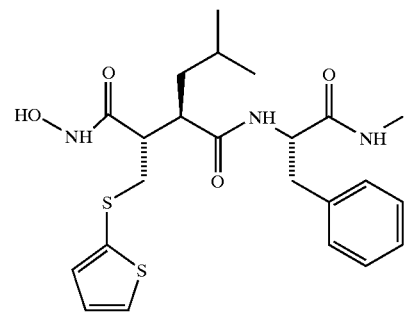

Batimastat (British Biotech)

-continued
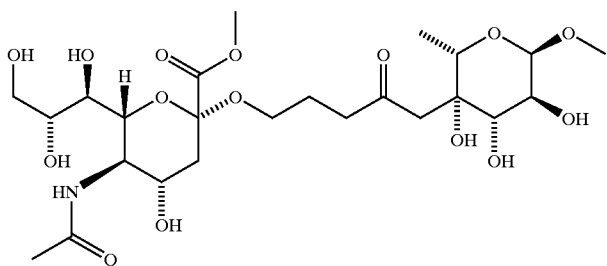
(British Biotech)
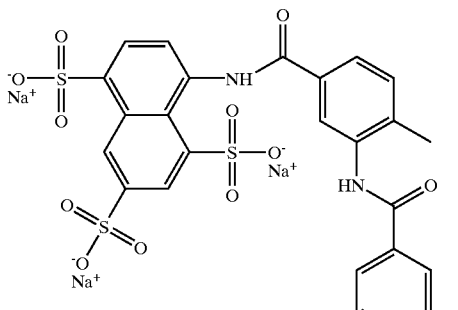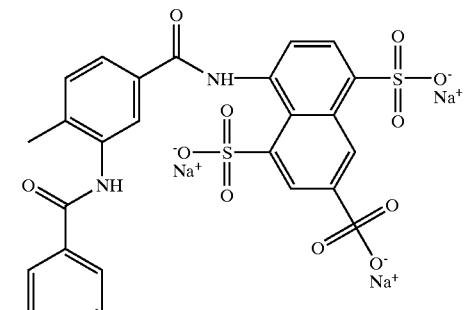
Suramin sodium (Parke-Davis)
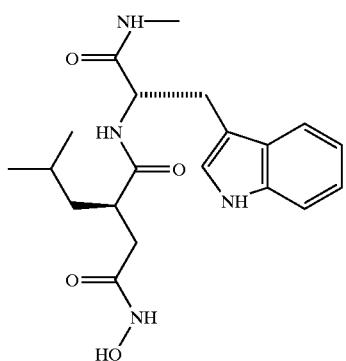
Galardin (Glycomed)
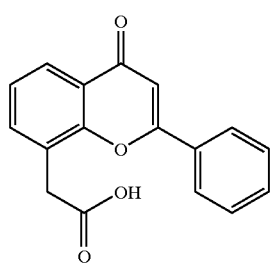
Mitoflaxone (lipha)
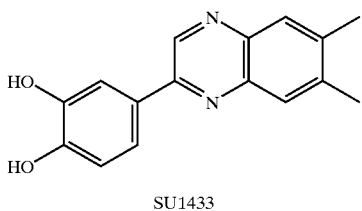
SU1433
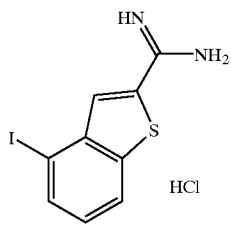
B-428 (Eisai) [uPA inhibitor]
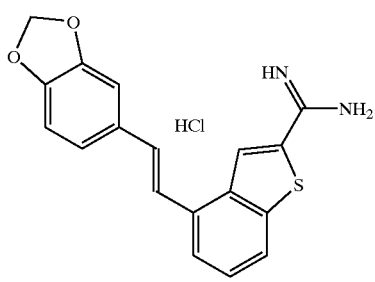
B-623 (Eisai) [uPA inhibitor]
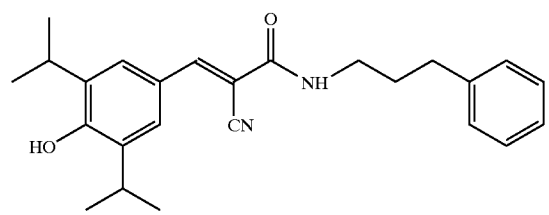
SU1498

Other known compounds capable of targeting regions of angiogenesis are listed in Table 4 below:

TABLE 4

Vector molecules with known affinity for receptors associated with angiogenesis
Vector Molecules angiopoietins
angiostatin [plasminogen fragment] [inhibitor]
angiotensin II
$\alpha_2$-antiplasmin
combinatorial libraries, compounds from
for instance compounds that bind to basement membrane after degradation
β-Cyclodextrin tetradecasulfate
endoglin
endosialin
endostatin [collagen fragment]
epidermal growth factor (heparin-binding)
fibrin
fibrinopeptide β
fibroblast growth factor, FGF-3, basic
fibronectin
fumagillin and analogs
heparin
hepatocyte growth factor
hyaluronan
insulin-like growth factor
interferon-α, β [inhibitors]
interleukins: IL-8, IL-12 [inhibitor]
laminin, laminin fraqments
leukemia inhibitory factor
linomide
matrix metalloproteinase-2
metalloproteinases
metalloproteinase inhibitors
monoclonal antibodies
for instance: to angiogenic factors or their receptors or
to components of the fibrinolytic system
peptides: for instance, cyclic $RGD_DFV$
placental growth factor
placental proliferin-related protein
plasminogen
plasminogen activator
plasminogen activator inhibitor-1
platelet activating factor antagonists [inhibitors]
platelet-derived growth factor (e.g. type BB)
platelet-derived growth factor receptors
platelet-derived endothelial cell growth factor
pleiotropin
proliferin, proliferin-related protein
selectins: E-selectin
SPARC
snake venoms (RGD-containing)
substance P (a neuropeptide: neurokinin)
suramin
tissue inhibitor of metalloproteinases (e.g. TIMP-2)
thalidomide
thrombin
thrombin-receptor-activating tetradecapeptide
transforming growth factor-α, β
transforming growth factor receptor
tumor growth factor-α

TABLE 4-continued

Vector molecules with known affinity for receptors associated with angiogenesis
Vector Molecules tumor necrosis factor
vitronectin note: many hormones, growth factors and other compounds which bind to cell surface receptors may act as vectors by binding to their receptors, or, when they are already bound to the cell surface, they are targets for vectors that bind to them, for instance antibodies.

Similarly the compounds described in WO95/08327 may be used as vectors (see also Kohn et al. Proc. Nat. Acad Sci. USA. 92: 1307–1311 (1995) and J. Clin. Oncol. 15: 1985–1993 (1997)).

Particular examples of vector compounds described in some of the patent publications mentioned above are as follows:

WO95/08327 (Dept. of Health and Human Services) describes angiogenesis inhibitor compounds of formula I and II:

$$Y-(CH_2)_p-Ar^1-X-Ar^2 \tag{I}$$

wherein
Ar$^1$ and Ar$^2$ are aromatic groups and may be different or the same; and X is a linking group eg. O, S, SO$_2$, CO, CHCN, alkyl, alkoxy or alkoxyalkyl, and

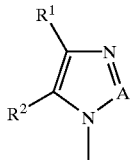

wherein
A is N or CH; R1 is H, —CONH, —CONHR$^5$, COOH, —COOR$^5$, SO$_2$NH$_2$; R2 is H, NH$_2$, NHCOPh, —NHCOR$^5$, —NHCHO, —NHR$^5$, —N(R$^5$)$_2$; and R$^5$ is alkyl with 1–6 carbons, e.g.

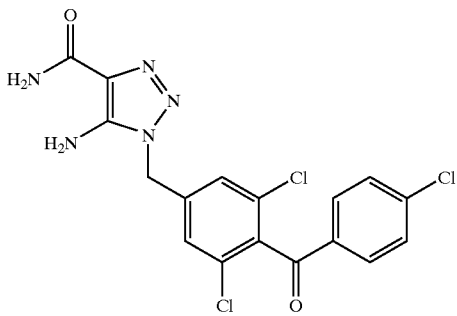

WO95/06473 (Nippon Kayaku Kabushiki Kasai) discloses antitumor and angiogenesis inhibitor compounds of formula 1 and 2:

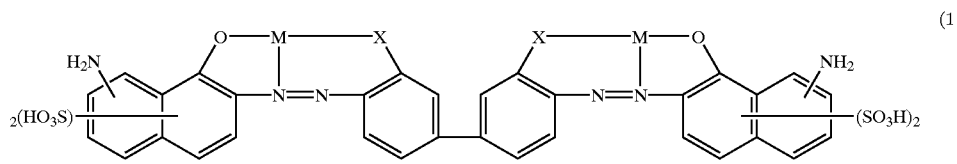

(1 wherein
X is O, COO; and M is a transition metal, and

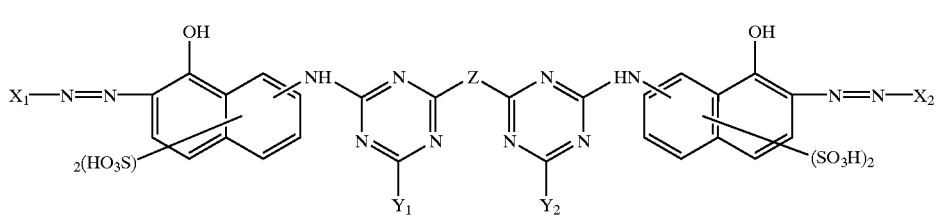

wherein
X₁ and X₂ are substituted or unsubstituted phenyl or naphthyl groups; Y₁ and Y₂ are halogen atoms, amino groups or mono- or di-substituted amino groups; and Z is $NHC_2H_4NH$ or a substituted or unsubstituted aromatic diamine residue e.g.

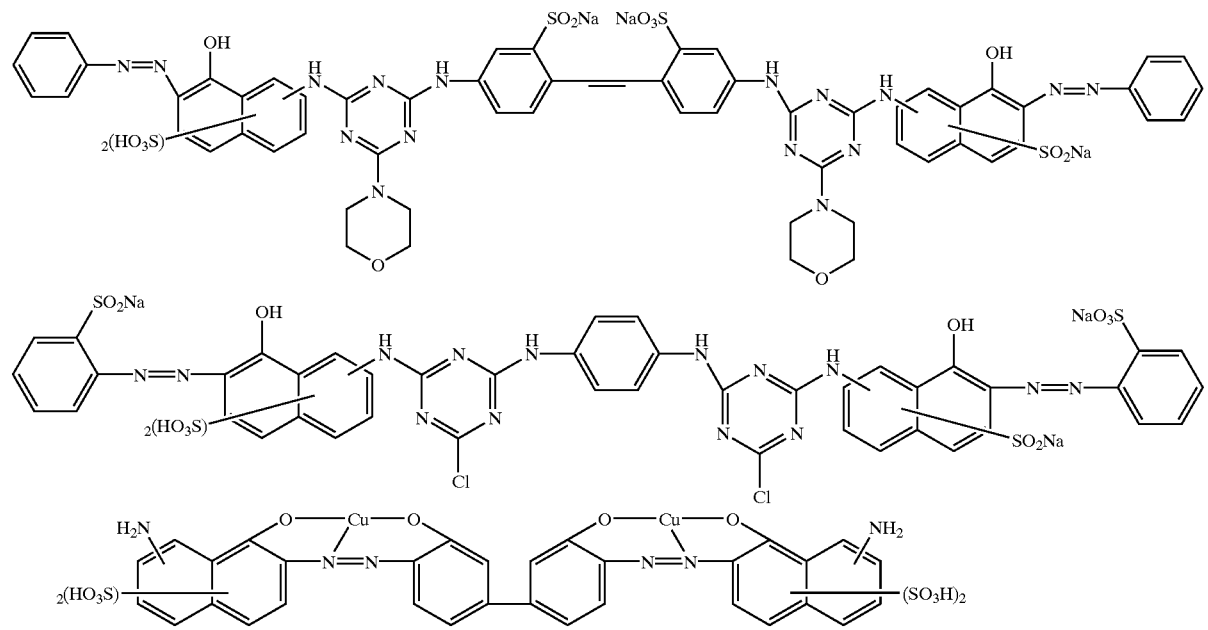

WO95/04033 (Celltech Limited) discloses the following angiogenesis inhibitors:

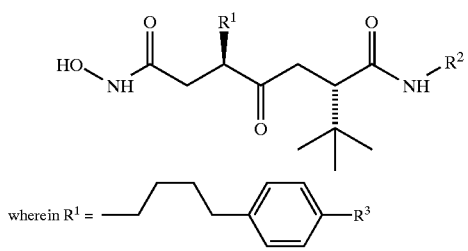

R3 is H, halogen or $CH_3$, $CF_3$ or $OCH_3$; R2 is H or $CH_3$ e.g. $N^4$-hydroxy-$N^1$-(1-(S)-carbamoyl-2,2-dimethylpropyl)-2-(R)-4(chlorophenyl-propyl)succinamide; $N^4$-hydroxy-$N^1$- (1-(S)-carbamoyl-2,2-dimethylpropyl)-2-(R)-(4-methylphenyl-propyl)succinamide; $N^4$-hydroxy-$N^1$-(1-(S)-carbamoyl-2,2-dimethylpropyl)-2-(R)-(4-methoxyphenyl-propyl) succinamide; and $N^4$-hydroxy-$N^1$- (1-(S)-carbamoyl-2,2-dimethylpropyl)-2-(R)-(4-trifluoromethyl-phenyl-propyl)-succinamide.

EP 241830 (The General Hospital Corporation) discloses purification of hepatoma-derived growth factor (HDGF), which is an endothelial mitogen and a potent angiogenic factor. The use of HDGF in controlling angiogenesis and detecting cancerous liver tumors by use of an immunodiagnostic assay is also disclosed. The HDGF peptide fragment has an N-terminal amino acid sequence wherein the first 16 amino acids are:

Sequence No. 1 Leu-Pro-Ala-Leu-Pro-Glu-Asp-Gly-Gly-xx-Gly-Ala-Phe-Pro-Pro-Gly (xx=unidentified amino acid moiety)

An HDGF peptide fragment is also disclosed which has an N-terminal amino acid extension sequence comprising:

Sequence No. 2 (ala/ser)-(leu/arg)-pro-(ala/gly)-(leu/pro)-ala-gly-thr-met-ala-(ala) gly-ser-(isoleu)-thr-thr-leu EP 652000 (Eli Lilly and Company) discloses angiogenesis inhibitor and angiogenic disease inhibitor compounds having the forumla:

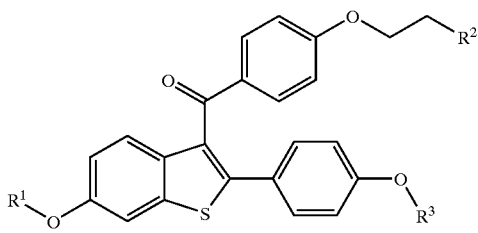

wherein
R1 and R3 are H, Me, —C(O) (C$_1$–C$_6$ alkyl), —C(O)Ar; Ar is optionally substituted phenyl; and R2 is pyrrolidino or piperidino, e.g.

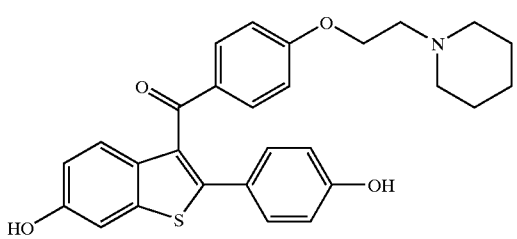

EP 652000 [589719?] (Eli Lilly and Company) discloses modified platelet factor-4 having the amino acid sequence:

Sequence No. 3 (MPF-4)
NH$_2$-Ser-Gln-Val-Arg-Pro-Arg-His-lle-Thr-Ser-Leu-Glu-Val-lle-Lys-Ala-Gly-Pro-His-Cys-Pro-Thr-Ala-Gln-Leu-lle-Ala-Thr-Leu-Lys-Asn-Gly-Arg-Lys-lle-Cys-Leu-Asp-Leu-Gln-Ala-Pro-Leu-Tyr-Lys-Lys-lle-lle-Lys-Lys-Leu-Leu-Glu-Ser-COOH Sequence No. 4 (CPF-4)
NH$_2$-Ser-Gln-Val-Arg-Pro-Arg-His-lle-Thr-Ser-Leu-Glu-Val-lle-Lys-Ala-Gly-Pro-His-Cys-Pro-Thr-Ala-Gln-Leu-lle-Ala-Thr-Leu-Lys-Asn-Gly-Arg-Lys-lle-Cys-Leu-Asp-Leu-Gln-Ala-Pro-Leu-Tyr-Lys-lle-le-Lys-Lys-Leu-Leu-Glu-Ser-COOH disulfide bonded to a second protein having the amino acid sequence.

Sequence No. 5
NH$_2$-Glu-Ala-Glu-Glu-Asp-Gly-Asp-Leu-Gln-Cys-Leu-Cys-Val-Lys-Thr-Thr-COOH. There are disulfide bridges between Cys-20 of MPF-4 and Cys-10 of the said second protein and between Cys-36 of MPF4 and Cys-12 of the said second protein.

WO94/13277 (Imperical Cancer Research Technology Limited) discloses the use of compounds of formula I:

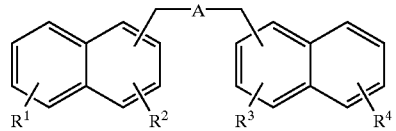

R1 to R4 are each independently one or more of —X, N$_3$, —NO$_2$, halo, trifluoromethyl, R$^5$, OR$^5$, —CH$_2$OR$^6$, —OCOR$^5$, —CH$_2$OCOR$^5$, —NHCOR$^5$, —CH$_2$NHCOR$^5$, —NR$^5$R$^6$, —CH$_2$NR$^5$R$^6$, —CH$_2$NO$_2$, CONR$^5$R$^6$, CH$_2$CONR$^5$R$^6$, —COOR$^5$, —CH$_2$COOR$^5$, —CHO and CH$_2$CHO and —X is independently —SO$_3$R$^5$, —CH$_2$PO$_3$R$^5$R$^6$, —CH$_2$SO$_3$R$^5$, —OSO$_3$R$^5$, —CH$_2$OSO$_3$R$^5$, —NHSO$_3$R$^5$, —CH$_2$NHSO$_3$R$^5$, OPO$_3$R$^5$R$^6$, —CH$_2$OPO$_3$R$^5$R$^6$ and —PO$_3$R$^5$R$^6$ where R$^5$ and R$^6$ are chosen independently from —H and lower alkyl and wherein A is a chemical group comprising at least 5 and no more than 30 bonds directly linking the naphthyl groups provided that (i) the compound is not suramin and (ii) when A is not

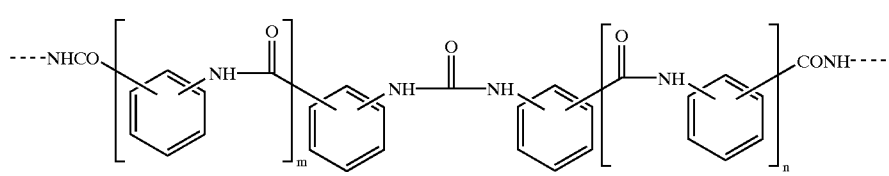

wherein
m and n are independently 0, 1 or 2, then at least one of R1 to R4 is —OH or an acidic group; and of the pharmaceutically acceptable salts, esters, salts of such esters or amides of such compounds.

Also described are compounds wherein the linkage of A to the naphthyl ring is via an amide or sulphonamide group. Furthermore A may in some cases be a group of formula II. A may also be selected from straight chain or branched alkyl groups, aryl groups, alkylaryl groups, aliphatic dicarboxylic acids, polyenes and derivatives thereof and polyols and derivatives thereof. Some further compounds are of formulae:

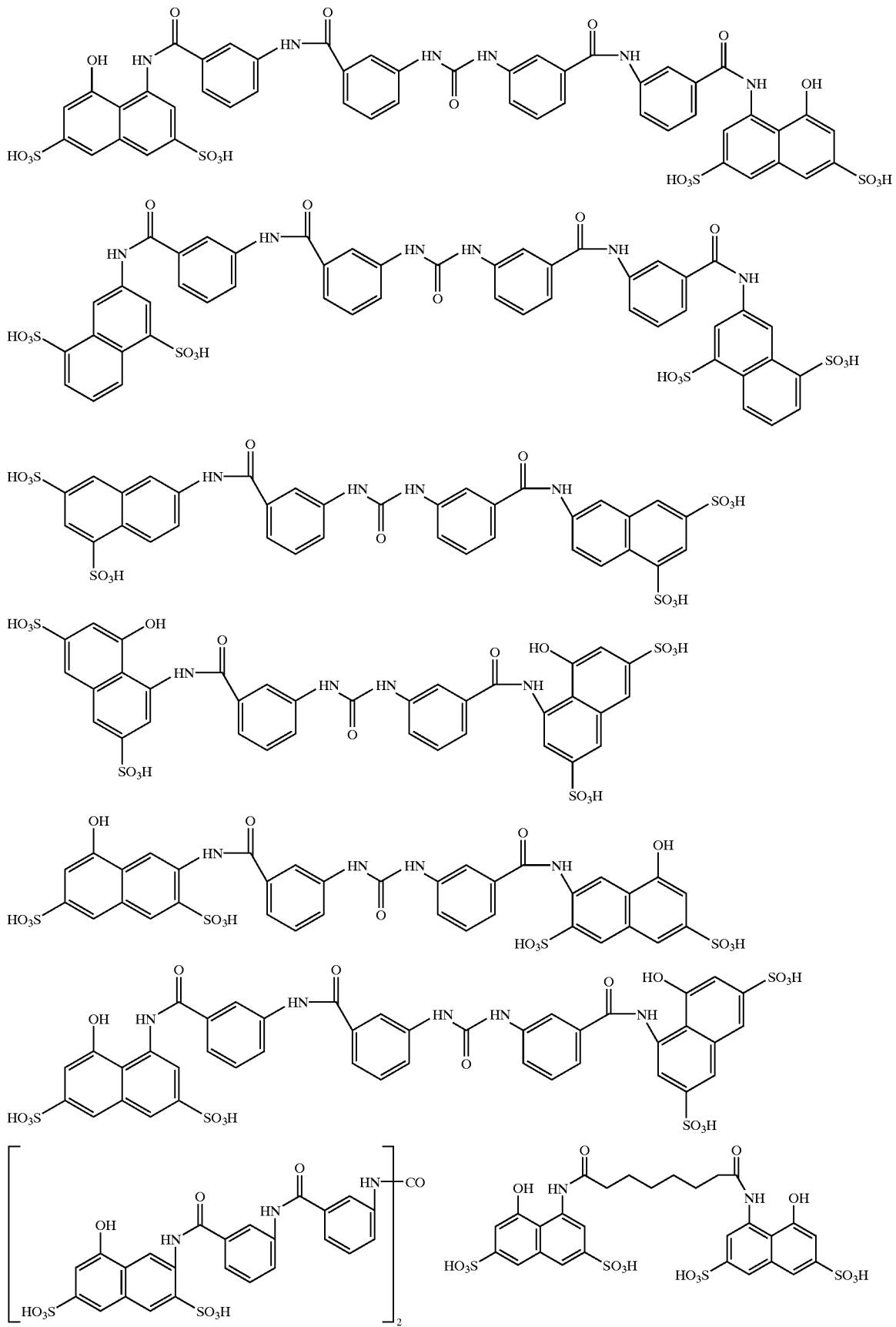

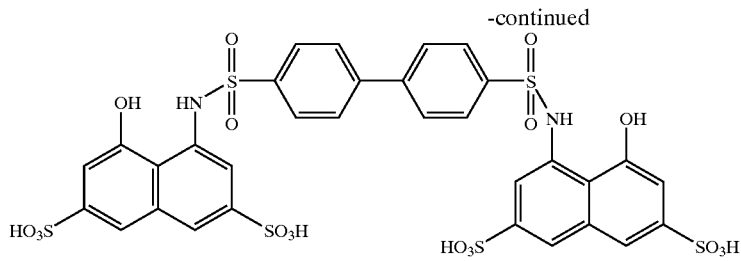
EP 678296 (Tsumura & Co.) discloses angiogenesis inhibitors of the general fomula:
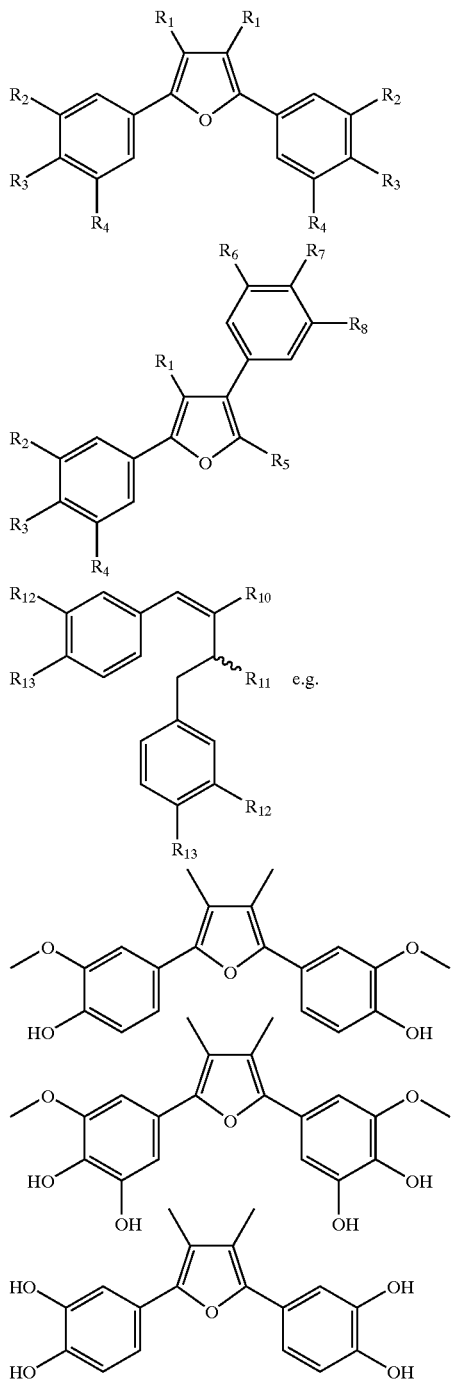
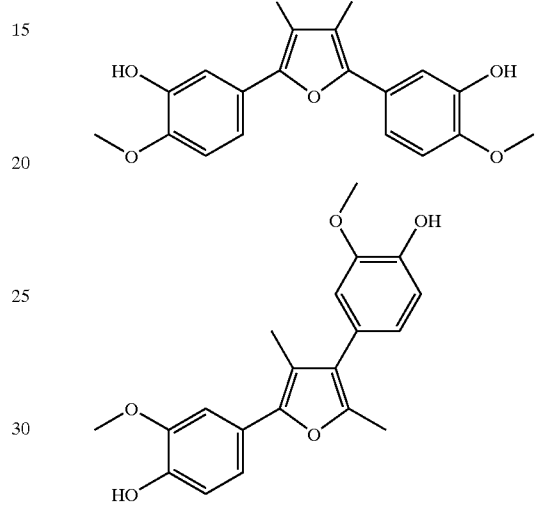
WO94/18967 (President and Fellows of Harvard College) discloses a class of imidazoles that inhibit angiogenesis:
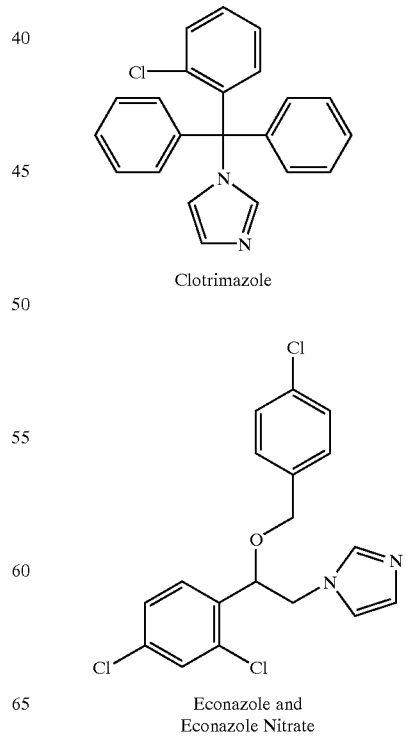

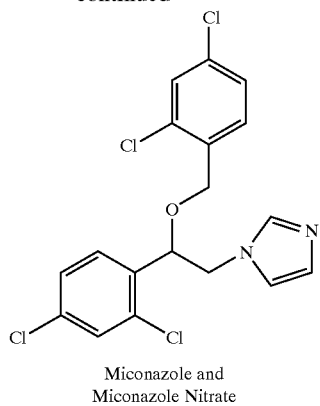
Miconazole and
Miconazole Nitrate
EP-A-618208 (Daiichi Pharmaceutical) discloses compounds of formula:
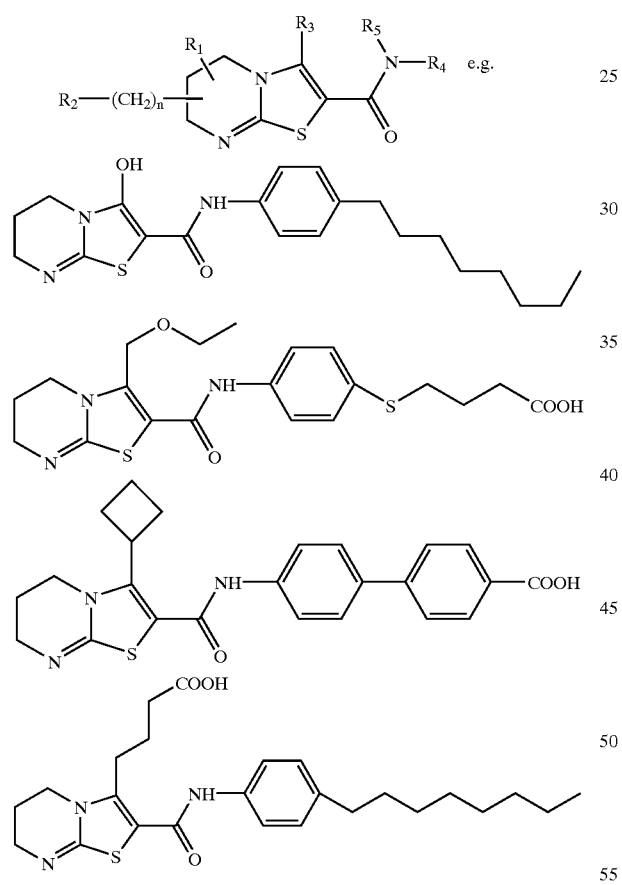
WO94/02446 (British Biotechnology Limited) discloses compounds of formula:
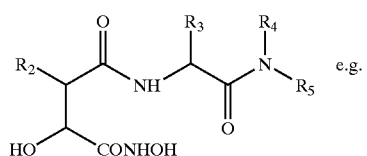
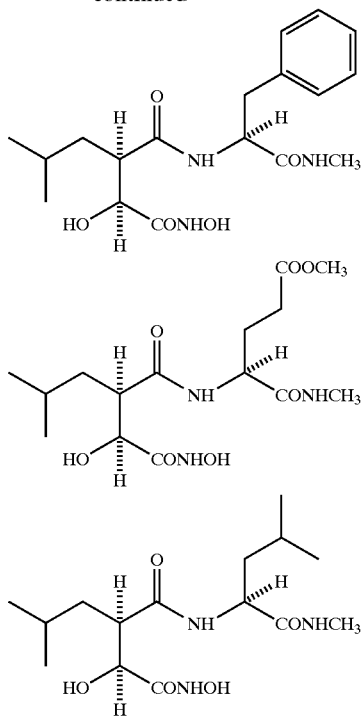
WO94/02447 (British Biotechnology Limited) discloses compounds of formula:
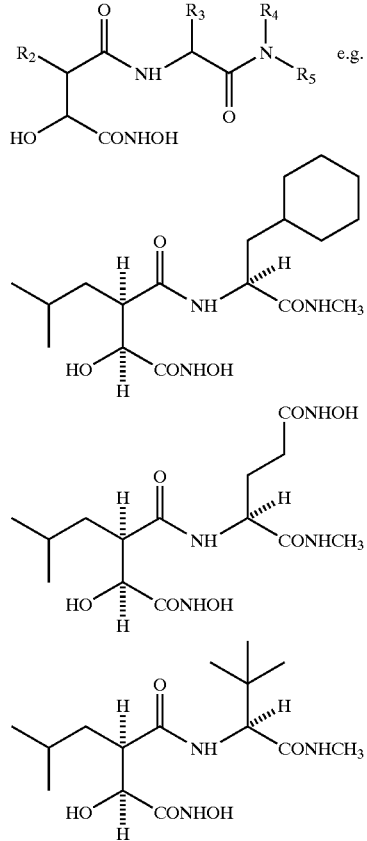

-continued
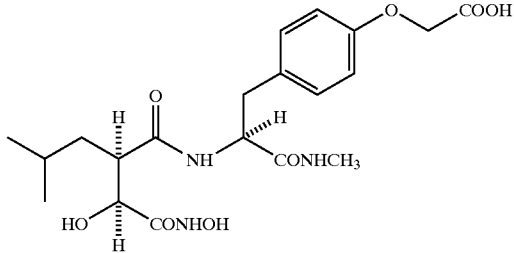
WO94/21625 (British Biotechnology Limited) discloses compounds of formula:
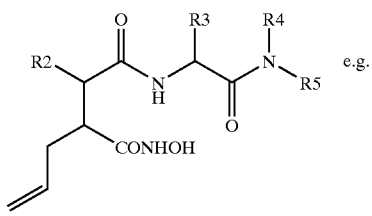
e.g.
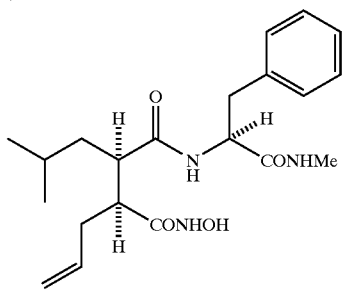
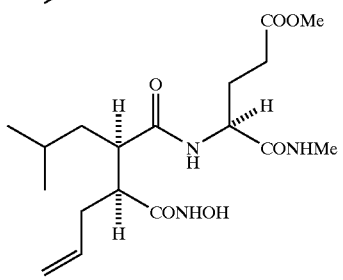
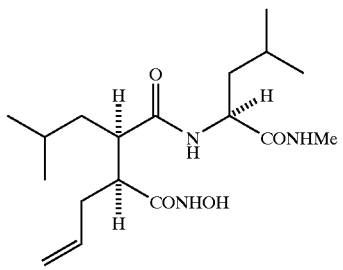
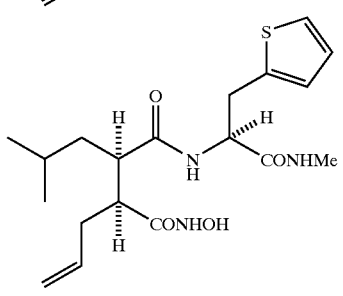
WO94/24149 (British Biotechnology Limited) discloses compounds of formula (I):
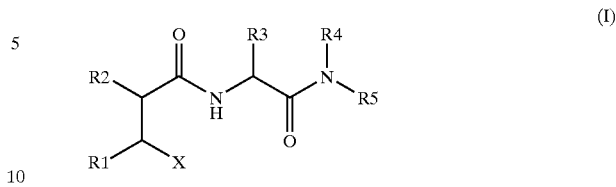
where in
X is —CONHOH or COOH, principally characterised by the presence in substituent R3 and/or R4 of a group of formula (II)
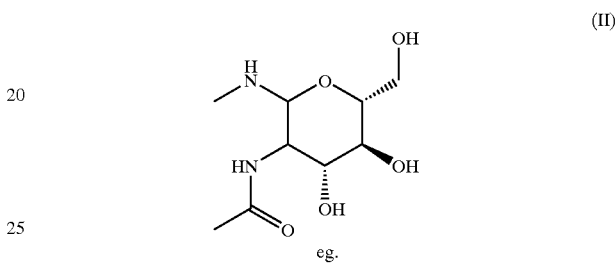
eg.
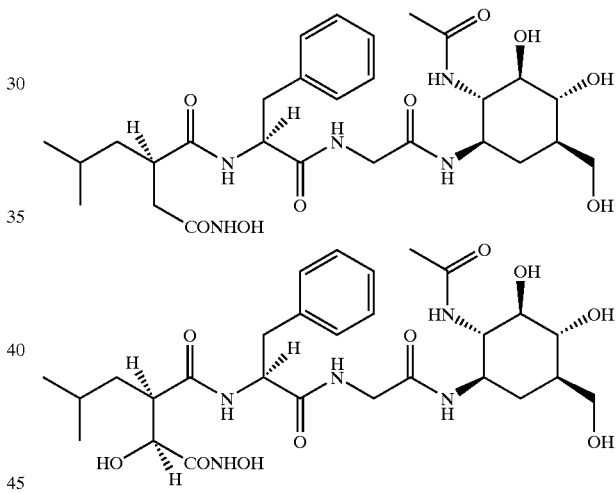
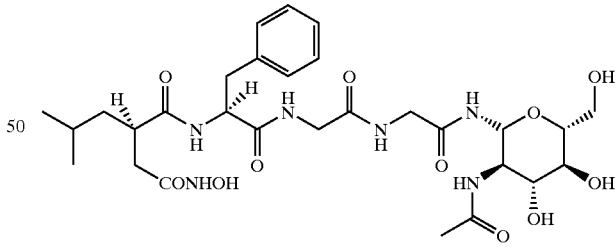
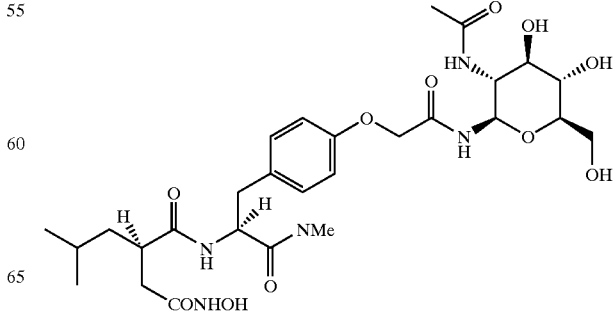

-continued

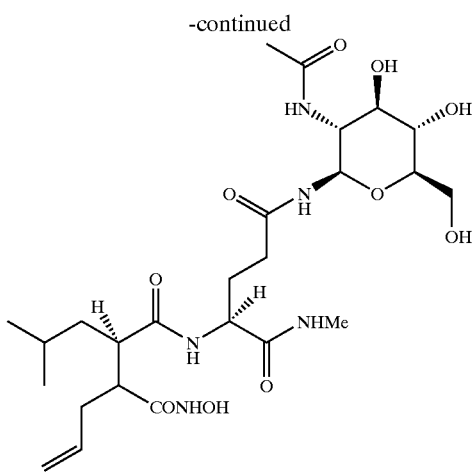

The contents of all the publications referred to herein is hereby incorporated by reference.

Particularly preferred vectors include amino acid derivatives such as described in WO94/02446, hydroxamic acid derivatives such as described in WO94/02447, thiazolopyrimidines such as described in EP-A-618208, triazoles such as described in WO95/08327, quinazolines such as described in WO97/30035, isoindolones such as described in WO97/37655, integrin inhibitors, VEGF antagonists, bFGF antagonists, thrombospondin and thrombospondin fragments, CD36 and growth factors (e.g. VEGF, bFGF, etc).

CAM-D and other candidate identification and evaluation techniques as mentioned above can also be used to find or assess further candidate peptidic and non-peptidic vectors.

Thus it is also possible to obtain molecules that bind specifically to angiogenesis associated receptors by direct screening of molecular libraries. Screening of peptidic libraries may also be used to identify generally effective peptidic structures of which non-peptidic analogs may be generated by conventional or combinatorial chemistry. Binding moieties identified in this way may be coupled to a linker molecule, constituting a general tool for attaching any vector molecule (or molecules) to the reporter.

Vector molecules may be generated from combinatorial libraries without necessarily knowing the exact molecular target, by functionally selecting (in vitro, ex vivo or in vivo) for molecules binding to the region/structure to be imaged.

As mentioned above, the agents of formula I comprise vector, linker and reporter moieties. A linker moiety may serve to link one vector to one reporter; alternatively it may link together more than vector and/or more than one reporter. Likewise a reporter or a vector may be linked to more than one linker. Use in this way of a plurality of reporters (eg. several linker-reporter moieties attached to one vector or several reporters attached to one linker itself attached to one vector) may enable the detectability of the contrast agent to be increased (eg. by increasing its radioopacity, echogenicity or relaxivity) or may enable it to be detected in more than one imaging modality. Use in this way of a plurality of vectors may increase the targeting efficiency of the contrast agent or may make the contrast agent able to target more than one site, eg. different receptors for an agent which has receptor heterogeneity. Thus for example the agent of formula I may include vector moieties with affinity sites other than angiogenesis associated receptors, eg. with affinities for cell surfaces on body duct wall surfaces. Accordingly, the agent may include vectors such as antibody fragments and oligopeptides, eg. containing RGD or analogous cell surface binding peptide motifs (for example as described in EP-A-422937 and EP-A-422938 (Merck)) or other vectors as described in GB 9700699.3. Such extra vectors may also be selected from any of the molecules that naturally concentrate in a selected target organ, tissue, cell or group of cells, or other location in a mammalian body, in vivo. These can include amino acids, oligopeptides (e.g. hexapeptides), molecular recognition units (MRU's), single chain antibodies (SCA's), proteins, non-peptide organic molecules, Fab fragments, and antibodies. Examples of site-directed molecules include polysaccharides (e.g. CCK and hexapeptides), proteins (such as lectins, asialofetuin, polyclonal IgG, blood clotting proteins (e.g. hirudin), lipoproteins and glycoproteins), hormones, growth factors, clotting factors (such as PF4), polymerized fibrin fragments (e.g., $E_1$), serum amyloid precursor (SAP) proteins, low density lipoprotein (LDL) precursors, serum albumin, surface proteins of intact red blood cells, receptor binding molecules such as estrogens, liver-specific proteins/polymers such as galactosyl-neoglycoalbumin (NGA) (see Vera et al. in Radiology 151: 191 (1984)) N-(2-hydroxy-propyl)methacrylamide (HMPA) copolymers with varying numbers of bound galactosamines (see Duncan et al., Biochim. Biophys. Acta 880:62 (1986)), and allyl and 6-aminohexyl glycosides (see Wong et al., Carbo. Res. 170:27 (1987)), and fibrinogen. The site-directed protein can also be an antibody. The choice of antibody, particularly the antigen specificity of the antibody, will depend on the particular intended target site for the agent. Monoclonal antibodies are preferred over polyclonal antibodies. Preparation of antibodies that react with a desired antigen is well known. Antibody preparations are available commercially from a variety of sources. Fibrin fragment $E_1$ can be prepared as described by Olexa et al. in J. Biol. Chem. 254:4925 (1979). Preparation of LDL precursors and SAP proteins is described by de Beer et al. in J. Immunol. Methods 50:17 (1982). The above described articles are incorporated herein by reference in their entirety.

It is especially preferred that such extra vectors should bind so as to slow but not prevent the motion of the agent in the bloodstream and to anchor it in place when it is bound to a receptor site associated with angiogenesis.

Functional groups (e.g. amino groups, hydroxyl groups, carboxy groups, thiol groups, etc) on the vector compound may be used for binding of the vector to the linker moiety or directly to the reporter moiety, e.g. using conventional chemical coupling techniques.

Where the vector is a peptidic compound, the reporter is a multireporter, e.g. a metallated polychelant (preferably a dendrimeric polychelant), a magnetic (preferably superparamagnetic) particle, a vesicle containing contrast effective particles or a solution of contrast effective molecule, a polyionic species (e.g. a polymer carrying a multiplicity of ionic groups, preferably anionic groups, e.g. a carboxylate, phosphate or sulphonate polymer).

Where the vector is non-peptidic, the reporter may be a multireporter or alternatively may comprise one or a small number (e.g. up to 10) of detectable labels, e.g. chelated paramagnetic metal ions, covalently bound or chelated radioisotopes, and chromophores (or fluorophores, etc). Where the reporter is or comprises a covalently bound radionuclide, this is preferably an iodine radionuclide rather than a tritium or $^{13}C$ atom Linker A wide variety of linkers can be used, including biodegradable linkers and biopolymers.

The linker component of the contrast agent is at its simplest a bond between the vector and reporter moieties. More generally however the linker will provide a mono- or multi-molecular skeleton covalently or non-covalently linking one or more vectors to one or more reporters, eg. a linear, cyclic, branched or reticulate molecular skeleton, or a molecular aggregate, with in-built or pendant groups which bind covalently or non-covalently, eg. coordinatively, with the vector and reporter moieties or which encapsulate, entrap or anchor such moieties.

Thus linking of a reporter unit to a desired vector may be achieved by covalent or non-covalent means, usually involving interaction with one or more functional groups located on the reporter and/or vector. Examples of chemically reactive functional groups which may be employed for this purpose include amino, hydroxyl, sulfhydryl, carboxyl, and carbonyl groups, as well as carbohydrate groups, vicinal diols, thioethers, 2-aminoalcohols, 2-aminothiols, guanidinyl, imidazolyl and phenolic groups.

Covalent coupling of reporter and vector may therefore be effected using linking agents containing reactive moities capable of reaction with such functional groups. Examples of reactive moieties capable of reaction with sulfhydryl groups include α-haloacetyl compounds of the type X—CH$_2$CO— (where X=Br, Cl or I), which show particular reactivity for sulfhydryl groups but which can also be used to modify imidazolyl, thioether, phenol and amino groups as described by Gurd, F. R. N. in *Methods Enzymol.* (1967) 11, 532. N-Maleimide derivatives are also considered selective towards sulfhydryl groups, but may additionaly be useful in coupling to amino groups under certain conditions. Reagents such as 2-iminothiolane, e.g. as described by Traut, R. et al. in Biochemistry (1973) 12, 3266, which introduce a thiol group through conversion of an amino group, may be considered as sulfhydryl reagents if linking occurs through the formation of disulphide bridges. Thus reagents which introduce reactive disulphide bonds into either the reporter or the vector may be useful, since linking may be brought about by disulphide exchange between the vector and reporter; examples of such reagents include Ellman's reagent (DTNB), 4,4'-dithiodipyridine, methyl-3-nitro-2-pyridyl disulphide and methyl-2-pyridyl disulphide (described by Kimura, T. et al. in *Analyt. Biochem.* (1982) 122, 271).

Examples of reactive moieties capable of reaction with amino groups include alkylating and acylating agents. Representative alkylating agents include:
i) α-haloacetyl compounds, which show specificity towards amino groups in the absence of reactive thiol groups and are of the type X—CH$_2$CO— (where X=Cl, Br or I), e.g. as described by Wong, Y-H. H. in *Biochemistry* (1979) 24, 5337;
ii) N-maleimide derivatives, which may react with amino groups either through a Michael type reaction or through acylation by addition to the ring carbonyl group as described by Smyth, D. G. et al. in *J. Am. Chem. Soc.* (1960) 82, 4600 and *Biochem. J.* (1964) 91, 589;
iii) aryl halides such as reactive nitrohaloaromatic compounds;
iv) alkyl halides as described by McKenzie, J. A. et al. in *J. Protein Chem.* (1988) 7, 581;
v) aldehydes and ketones capable of Schiff's base formation with amino groups, the adducts formed usually being stabilised through reduction to give a stable amine;
vi) epoxide derivatives such as epichlorohydrin and bisoxiranes which may react with amino, sulfhydryl or phenolic hydroxyl groups;
vii) chlorine-containing derivatives of s-triazines, which are very reactive towards nucleophiles such as amino, sufhydryl and hydroxy groups;
viii) aziridines based on s-triazine compounds dET$_A$iled above, e.g. as described by Ross, W. C. J. in *Adv. Cancer Res.* (1954) 2, 1, which react with nucleophiles such as amino groups by ring opening;
ix) squaric acid diethyl esters as described by Tietze, L. F. in *Chem. Ber.* (1991) 124, 1215; and
x) α-haloalkyl ethers, which are more reactive alkylating agents than normal alkyl halides because of the activation caused by the ether oxygen atom, e.g. as described by Benneche, T. et al. in *Eur. J. Med. Chem.* (1993) 28, 463.

Representative amino-reactive acylating agents include:
i) isocyanates and isothiocyanates, particularly aromatic derivatives, which form stable urea and thiourea derivatives respectively and have been used for protein crosslinking as described by Schick, A. F. et al. in *J. Biol. Chem.* (1961) 236, 2477;
ii) sulfonyl chlorides, which have been described by Herzig, D. J. et al. in Biopolymers (1964) 2, 349 and which may be useful for the introduction of a fluorescent reporter group into the linker;
iii) Acid halides;
iv) Active esters such as nitrophenylesters or N-hydroxysuccinimidyl esters;
v) acid anhydrides such as mixed, symmetrical or N-carboxyanhydrides;
vi) other useful reagents for amide bond formation as described by Bodansky, M. et al. in '*Principles of Peptide Synthesis*' (1984) Springer-Verlag;
vii) acylazides, e.g. wherein the azide group is generated from a preformed hydrazide derivative using sodium nitrite, e.g. as described by Wetz, K. et al. in *Anal. Biochem.* (1974) 58, 347;
viii) azlactones attached to polymers such as bis-acrylamide, e.g. as described by Rasmussen, J. K. in Reactive Polymers (1991) 16, 199; and
ix) Imidoesters, which form stable amidines on reaction with amino groups, e.g. as described by Hunter, M. J. and Ludwig, M. L. in J. Am. Chem. Soc. (1962) 84, 3491.

Carbonyl groups such as aldehyde functions may be reacted with weak protein bases at a pH such that nucleophilic protein side-chain functions are protonated. Weak bases include 1,2-aminothiols such as those found in N-terminal cysteine residues, which selectively form stable 5-membered thiazolidine rings with aldehyde groups, e.g. as described by Ratner, S. et al. in *J. Am. Chem. Soc.* (1937) 59, 200. Other weak bases such as phenyl hydrazones may be used, e.g. as described by Heitzman, H. et al. in *Proc. Natl. Acad. Sci. USA* (1974) 71, 3537.

Aldehydes and ketones may also be reacted with amines to form Schiff's bases, which may advantageously be stabilised through reductive amination. Alkoxylamino moieties readily react with ketones and aldehydes to produce stable alkoxamines, e.g. as described by Webb, R. et al. in *Bioconjugate Chem.* (1990) 1, 96.

Examples of reactive moieties capable of reaction with carboxyl groups include diazo compounds such as diazoacetate esters and diazoacetamides, which react with high specificity to generate ester groups, e.g. as described by Herriot R. M. in *Adv. Protein Chem.* (1947) 3, 169. Carboxylic acid modifying reagents such as carbodiimides, which react through O-acylurea. formation followed by amide bond formation, may also usefully be employed; linking may be facilitated through addition of an amine or may result in direct vector-receptor coupling. Useful water soluble carbodiimides include 1-cyclohexyl-3-(2-morpholinyl-4-ethyl)carbodiimide (CMC) and 1-ethyl-3-(3-dimethylaminopropyl)carbodiimide (EDC), e.g. as described by Zot, H. G. and Puett, D. in *J. Biol. Chem.* (1989) 264, 15552. Other useful carboxylic acid modifying reagents include isoxazolium derivatives such as Woodwards reagent K; chloroformates such as p-nitrophenylchloroformate; carbonyldiimidazoles such as 1,1'-carbonyldiimidazole; and N-carbalkoxydihydroquinolines such as N-(ethoxycarbonyl)-2-ethoxy-1,2-dihydroquinoline.

Other potentially useful reactive moieties include vicinal diones such as p-phenylenediglyoxal, which may be used to react with guanidinyl groups, e.g. as described by Wagner et al. in *Nucleic acid Res.* (1978) 5, 4065; and diazonium salts, which may undergo electrophilic substitution reactions, e.g. as described by Ishizaka, K. and Ishizaka T. in J. Immunol. (1960) 85, 163. Bis-diazonium compounds are readily prepared by treatment of aryl diamines with sodium nitrite in acidic solutions. It will be appreciated that functional groups in the reporter and/or vector may if desired be converted to other functional groups prior to reaction, e.g. to confer additional reactivity or selectivity. Examples of methods useful for this purpose include conversion of amines to carboxylic acids using reagents such as dicarboxylic anhydrides; conversion of amines to thiols using reagents such as N-acetylhomocysteine thiolactone, S-acetylmercaptosuccinic anhydride, 2-iminothiolane or thiol-containing succinimidyl derivatives; conversion of thiols to carboxylic acids using reagents such as α-haloacetates; conversion of thiols to amines using reagents such as ethylenimine or 2-bromoethylamine; conversion of carboxylic acids to amines using reagents such as carbodiimides followed by diamines; and conversion of alcohols to thiols using reagents such as tosyl chloride followed by transesterification with thioacetate and hydrolysis to the thiol with sodium acetate.

Vector-reporter coupling may also be effected using enzymes as zero-length crosslinking agents; thus, for example, transglutaminase, peroxidase and xanthine oxidase have been used to produce crosslinked products. Reverse proteolysis may also be used for crosslinking through amide bond formation.

Non-covalent vector-reporter coupling may, for example, be effected by electrostatic charge interactions, through chelation in the form of stable metal complexes or through high affinity binding interaction.

A vector which is coupled to a peptide, lipo-oligosaccharide or lipopeptide linker which contains a element capable of mediating membrane insertion may also be useful. One example is described by Leenhouts, J. M. et al. in *Febs Letters* (1995) 370(3), 189–192.

Coupling may also be effected using avidin or streptavidin, which have four high-affinity binding sites for biotin. Avidin may therefore be used to conjugate vector to reporter if both vector and reporter are biotinylated. Examples are described by Bayer, E. A. and Wilchek, M. in *Methods Biochem. Anal.* (1980) 26, 1. This method may also be extended to include linking of reporter to reporter, a process which may encourage association of the agent and consequent potentially increased efficacy. Alternatively, avidin or streptavidin may be attached directly to the surface of reporter particles.

Non-covalent coupling may also utilise the bifunctional nature of bispecific immunoglobulins. These molecules can specifically bind two antigens, thus linking them. For example, either bispecific IgG or chemically engineered bispecific F(ab)'$_2$ fragments may be used as linking agents. Heterobifunctional bispecific antibodies have also been reported for linking two different antigens, e.g. as described by Bode, C. et al. in *J. Biol. Chem.* (1989) 264, 944 and by Staerz, U. D. et al. in *Proc. Natl. Acad. Sci. USA* (1986) 83, 1453. Similarly, any reporter and/or vector containing two or more antigenic determinants (e.g. as described by Chen, Aa et al. in *Am. J. Pathol.* (1988) 130, 216) may be crosslinked by antibody molecules and lead to formation of cross-linked assemblies of agents of formula I of potentially increased efficacy.

So-called zero-length linking agents, which induce direct covalent joining of two reactive chemical groups without introducing additional linking material (e.g. as in amide bond formation induced using carbodiimides or enzymatically) may, if desired, be used in accordance with the invention, as may agents such as biotin/avidin systems which induce non-covalent reporter-vector linking and agents which induce electrostatic interactions.

Most commonly, however, the linking agent will comprise two or more reactive moieties, e.g. as described above, connected by a spacer element. The presence of such a spacer permits bifunctional linkers to react with specific functional groups within a molecule or between two different molecules, resulting in a bond between these two components and introducing extrinsic linker-derived material into the reporter-vector conjugate. The reactive moieties in a linking agent may be the same (homobifunctional agents) or different (heterobifunctional agents or, where several dissimilar reactive moieties are present, heteromultifunctional agents), providing a diversity of potential reagents that may bring about covalent bonding between any chemical species, either intramolecularly or intermolecularly.

The nature of extrinsic material introduced by the linking agent may have a critical bearing on the targeting ability and general stability of the ultimate product. Thus it may be desirable to introduce labile linkages, e.g. containing spacer arms which are biodegradable or chemically sensitive or which incorporate enzymatic cleavage sites. Alternatively the spacer may include polymeric components, e.g. to act as surfactants and enhance the stability of the agent. The spacer may also contain reactive moieties, e.g. as described above to enhance surface crosslinking.

Spacer elements may typically consist of aliphatic chains which effectively separate the reactive moieties of the linker by distances of between 5 and 30 Å. They may also comprise macromolecular structures such as poly(ethylene glycols). Such polymeric structures, hereinafter referred to as PEGS, are simple, neutral polyethers which have been given much attention in biotechnical and biomedical applications (see e.g. Milton Harris, J. (ed) *"Poly(ethylene glycol) chemistry, biotechnical and biomedical applications"* Plenum Press, New York, 1992). PEGs are soluble in most solvents, including water, and are highly hydrated in aqueous environments, with two or three water molecules bound to each ethylene glycol segment; this has the effect of preventing adsorption either of other polymers or of proteins onto PEG-modified surfaces. PEGs are known to be nontoxic and not to harm active proteins or cells, whilst covalently linked PEGs are known to be non-immunogenic and non-antigenic. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes.

Appropriate molecular weights for PEG spacers used in accordance with the invention may, for example, be between 120 Daltons and 20 kDaltons.

The major mechanism for uptake of particles by the cells of the reticuloendothelial system (RES) is opsonisation by plasma proteins in blood; these mark foreign particles which are then taken up by the RES. The biological properties of PEG spacer elements used in accordance with the invention may serve to increase the circulation time of the agent in a similar manner to that observed for PEGylated liposomes (see e.g. Klibanov, A. L. et al. in *FEBS Letters* (1990) 268, 235–237 and Blume, G. and Cevc, G. in *Biochim. Biophys. Acta* (1990) 1029, 91–97). Increased coupling efficiency to areas of interest may also be achieved using antibodies bound to the terminii of PEG spacers (see e.g. Maruyama, K. et al. in *Biochim. Biophys. Acta* (1995) 1234, 74–80 and Hansen, C. B. et al. in *Biochim. Biophys. Acta* (1995) 1239, 133–144).

Other representative spacer elements include structural-type polysaccharides such as polygalacturonic acid, glycosaminoglycans, heparinoids, cellulose and marine polysaccharides such as alginates, chitosans and carrageenans; storage-type polysaccharides such as starch, glycogen, dextran and aminodextrans; polyamino acids and methyl and ethyl esters thereof, as in homo- and co-polymers of lysine, glutamic acid and aspartic acid; and polypeptides, oligosaccharides and oligonucleotides, which may or may not contain enzyme cleavage sites.

In general, spacer elements may contain cleavable groups such as vicinal glycol, azo, sulfone, ester, thioester or disulphide groups. Spacers containing biodegradable methylene diester or diamide groups of formula

[where X and Z are selected from. —O—, —S—, and —NR— (where R is hydrogen or an organic group); each Y is a carbonyl, thiocarbonyl, sulphonyl, phosphoryl or similar acid-forming group: m and n are each zero or 1; and $R^1$ and $R^2$ are each hydrogen, an organic group or a group —X.Y.$(Z)_m$—, or together form a divalent organic group] may also be useful; as discussed in, for example, WO-A-9217436 such groups are readily biodegraded in the presence of esterases, e.g. in vivo, but are stable in the absence of such enzymes. They may therefore advantageously be linked to therapeutic agents to permit slow release thereof.

Poly[N-(2-hydroxyethyl)methacrylamides] are potentially useful spacer materials by virtue of their low degree of interaction with cells and tissues (see e.g. Volfová, I., Ríhov á, B. and V. R. and Vetvicka, P. in *J. Bioact. Comp. Polymers* (1992) 7, 175–190). Work on a similar polymer consisting mainly of the closely related 2-hydroxypropyl derivative showed that it was endocytosed by the mononuclear phagocyte system only to a rather low extent (see Goddard, P., Williamson, I., Bron, J., Hutchkinson, L. E., Nicholls, J. and Petrak, K. in *J. Bioct. Compat. Polym.* (1991) 6, 4–24.).

Other potentially useful poymeric spacer materials include:

i) copolymers of methyl methacrylate with methacrylic acid; these may be erodible (see Lee, P. I. in *Pharm. Res.* (1993) 10, 980) and the carboxylate substituents may cause a higher degree of swelling than with neutral polymers;

ii) block copolymers of polymethacrylates with biodegradable polyesters (see e.g. San Roman, J. and Guillen-Garcia, P. in *Biomaterials* (1991) 12, 236–241);

iii) cyanoacrylates, i.e. polymers of esters of 2-cyanoacrylic acid—these are biodegradable and have been used in the form of nanoparticles for selective drug delivery (see Forestier, F., Gerrier, P., Chaumard, C., Quero, A. M., Couvreur, P. and Labarre, C. in *J. Antimicrob. Chemoter.* (1992) 30, 173–179);

iv) polyvinyl alcohols, which are water-soluble and generally regarded as biocompatible (see e.g. Langer, R. in *J. Control. Release* (1991) 16, 53–60);

v) copolymers of vinyl methyl ether with maleic anhydride, which have been stated to be bioerodible (see Finne, U., Hannus, M. and Urtti, A. in Int. *J. Pharm.* (1992) 78. 237–241);

vi) polyvinylpyrrolidones, e.g. with molecular weight less than about 25,000, which are rapidly filtered by the kidneys (see Hespe, W., Meier, A. M. and Blankwater, Y. M. in *Arzeim.-Forsch./Drug Res.* (1977) 27, 1158–1162);

vii) polymers and copolymers of short-chain aliphatic hydroxyacids such as glycolic, lactic, butyric, valeric and caproic acids (see e.g. Carli, F. in *Chim. Ind.* (Milan) (1993) 75, 494–9), including copolymers which incorporate aromatic hydroxyacids in order to increase their degradation rate (see Imasaki, K., Yoshida, M., Fukuzaki, H., Asano, M., Kumakura, M., Mashimo, T., Yamanaka, H. and Nagai. T. in Int. *J. Pharm.* (1992) 81, 31–38);

viii) polyesters consisting of alternating units of ethylene glycol and terephthalic acid, e.g. Dacron$^R$, which are non-degradable but highly biocompatible;

ix) block copolymers comprising biodegradable segments of aliphatic hydroxyacid polymers (see e.g. Younes, H., Nataf, P. R., Cohn, D., Appelbaum, Y. J., Pizov, G. and Uretzky, G. in *Biomater. Artif. Cells Artif. Organs* (1988) 16, 705–719), for instance in conjunction with polyurethanes (see Kobayashi, H., Hyon, S. H. and Ikada, Y. in "Water-curable and biodegradable prepolymers" *J. Biomed. Mater. Res.* (1991) 25, 1481–1494);

x) polyurethanes, which are known to be well-tolerated in implants, and which may be combined with flexible "soft" segments, e.g. comprising poly(tetra methylene glycol), poly(propylene glycol) or poly(ethylene glycol)) and aromatic "hard" segments, e.g. comprising 4,4'-methylenebis (phenylene isocyanate) (see e.g. Ratner, B. D., Johnston, A. B. and Lenk, T. J. in *J. Biomed. Mater. Res: Applied Biomaterials* (1987) 21, 59–90; Sa Da Costa, V. et al. in *J. Coll. Interface Sci.* (1981) 80, 445–452 and Affrossman, S. et al. in Clinical Materials (1991) 8, 25–31);

xi) poly(1,4-dioxan-2-ones), which may be regarded as biodegradable esters in view of their hydrolysable ester linkages (see e.g. Song, C. X., Cui, X. M. and Schindler, A. in *Med. Biol. Eng. Comput.* (1993) 31, S147–150), and which may include glycolide units to improve their absorbability (see Bezwada, R. S., Shalaby, S. W. and Newman, H. D. J. in *Agricultural and synthetic polymers: Biodegradability and utilization* (1990) (ed Glass, J. E. and Swift, G.), 167–174—ACS symposium Series, #433, Washington D.C., U.S.A.—American Chemical Society);

xii) polyanhydrides such as copolymers of sebacic acid (octanedioic acid) with bis(4-carboxy-phenoxy)propane, which have been shown in rabbit studies (see Brem, H., Kader, A., Epstein, J. I., Tamargo, R. J., Domb, A., Langer, R. and Leong, K. W. in *Sel. Cancer Ther*. (1989) 5, 55–65) and rat studies (see Tamargo, R. J., Epstein, J. I., Reinhard, C. S., Chasin, M. and Brem, H. in *J. Biomed. Mater. Res.* (1989) 23, 253–266) to be useful for controlled release of drugs in the brain without evident toxic effects;

xiii) biodegradable polymers containing ortho-ester groups, which have been employed for controlled release in vivo (see Maa, Y. F. and Heller, J. in *J. Control. Release* (1990) 14, 21–28); and xiv) polyphosphazenes, which are inorganic polymers consisting of alternate phosphorus and nitrogen atoms (see Crommen, J. H., Vandorpe, J. and Schacht, E. H. in *J. Control. Release* (1993) 24, 167–180).

The following tables list linking agents which may be useful in targetable agents in accordance with the invention.

Heterobifunctional linking agents

| Linking agent | Reactivity 1 | Reactivity 2 | Comments |
|---|---|---|---|
| ABH | carbohydrate | photoreactive | |
| ANB-NOS | —NH₂ | photoreactive | |
| APDP(1) | —SH | photoreactive | iodinable disulphide linker |
| APG | —NH₂ | photoreactive | reacts selectively with Arg at pH 7–8 |
| ASIB(1) | —SH | photoreactive | iodinable |
| ASBA(1) | —COOH | photoreactive | iodinable |
| EDC | —NH₂ | —COOH | zero-length linker |
| GMBS | —NH₂ | —SH | |
| sulfo-GMBS | —NH₂ | —SH | water-soluble |
| HSAB | —NH₂ | photoreactive | |
| sulfo-HSAB | —NH₂ | photoreactive | water-soluble |
| MBS | —NH₂ | —SH | |
| sulfo-MBS | —NH₂ | —SH | water-soluble |
| M₂C₂H | carbohydrate | —SH | |
| MPBH | carbohydrate | —SH | |
| NHS-ASA(1) | —NH₂ | photoreactive | iodinable |
| sulfo-NHS-ASA(1) | —NH₂ | photoreactive | water-soluble, iodinable |
| sulfo-NHS-LC-ASA(1) | —NH₂ | photoreactive | water-soluble, iodinable |
| PDPH | carbohydrate | —SH | disulphide linker |
| PNP-DTP | —NH₂ | photoreactive | |
| SADP | —NH₂ | photoreactive | disulphide linker |
| sulfo-SADP | —NH₂ | photoreactive | water-soluble disulphide linker |
| SAED | —NH₂ | photoreactive | disulphide linker |
| SAND | —NH₂ | photoreactive | water-soluble disulphide linker |
| SANPAH | —NH₂ | photoreactive | |
| sulfo-SANPAH | —NH₂ | photoreactive | water-soluble |
| SASD(1) | —NH₂ | photoreactive | water-soluble iodinable disulphide linker |
| SIAB | —NH₂ | —SH | |
| sulfo-SIAB | —NH₂ | —SH | water-soluble |
| SMCC | —NH₂ | —SH | |
| sulfo-SMCC | —NH₂ | —SH | water-soluble |
| SMPB | —NH₂ | —SH | |
| sulfo-SMPB | —NH₂ | —SH | water-soluble |
| SMPT | —NH₂ | —SH | |
| sulfo-LC-SMPT | —NH₂ | —SH | water-soluble |
| SPDP | —NH₂ | —SH | |
| sulfo-SPDP | —NH₂ | —SH | water-soluble |
| sulfo-LC-SPDP | —NH₂ | —SH | water-soluble |
| sulfo-SAMCA(2) | —NH₂ | photoreactive | |
| sulfo-SAPB | —NH₂ | photoreactive | water-soluble |

Notes:
(1) = iodinable;
(2) = fluorescent

Homobifunctional linking agents

| Linking agent | Reactivity | Comments |
|---|---|---|
| BS | —NH₂ | |
| BMH | —SH | |
| BASED (1) | photoreactive | iodinable disulphide linker |
| BSCOES | —NH₂ | |
| sulfo-BSCOES | —NH₂ | water-soluble |
| DFDNB | —NH₂ | |
| DMA | —NH₂ | |
| DMP | —NH₂ | |
| DMS | —NH₂ | |
| DPDPB | —SH | disulphide linker |
| DSG | —NH₂ | |
| DSP | —NH₂ | disulphide linker |
| DSS | —NH₂ | |
| DST | —NH₂ | |
| sulfo-DST | —NH₂ | water-soluble |
| DTBP | —NH₂ | disulphide linker |
| DTSSP | —NH₂ | disulphide linker |
| EGS | —NH₂ | |
| sulfo-EGS | —NH₂ | water-soluble |
| SPBP | —NH₂ | |

Biotinylation agents

| Agent | Reactivity | Comments |
|---|---|---|
| biotin-BMCC | —SH | |
| biotin-DPPE* | | preparation of biotinylated liposomes |
| biotin-LC-DPPE* | | preparation of biotinylated liposomes |
| biotin-HPDP | —SH | disulphide linker |
| biotin-hydrazide | carbohydrate | |
| biotin-LC-hydrazide | carbohydrate | |
| iodoacetyl-LC-biotin | —NH₂ | |
| NHS-iminobiotin | —NH₂ | reduced affinity for avidin |
| NHS-SS-biotin | —NH₂ | disulphide linker |
| photoactivatable biotin | nucleic acids | |
| sulfo-NHS-biotin | —NH₂ | water-soluble |
| sulfo-NHS-LC-biotin | —NH₂ | |

Notes:
DPPE = dipalmitoylphosphatidylethanolamine; LC = long chain

Agents for protein modification

| Agent | Reactivity | Function |
|---|---|---|
| Ellman's reagent | —SH | quantifies/detects/protects |
| DTT | —S.S— | reduction |
| 2-mercaptoethanol | —S.S— | reduction |
| 2-mercaptylamine | —S.S— | reduction |
| Traut's reagent | —NH₂ | introduces —SH |
| SATA | —NH₂ | introduces protected —SH |
| AMCA-NHS | —NH₂ | fluorescent labelling |
| AMCA-hydrazide | carbohydrate | fluorescent labelling |
| AMCA-HPDP | —S.S— | fluorescent labelling |
| SBF-chloride | —S.S— | fluorescent detection of —SH |
| N-ethylmaleimide | —S.S— | blocks —SH |
| NHS-acetate | —NH₂ | blocks and acetylates —NH₂ |
| citraconic anhydride | —NH₂ | reversibly blocks and introduces negative charges |
| DTPA | —NH₂ | introduces chelator |
| BNPS-skatole | tryptophan | cleaves tryptophan residue |
| Bolton-Hunter para-iodophenylalanine | —NH₂ | introduces iodinable group |

In addition to the already contemplated straight chain and branched PEG-like linkers (e.g polyethylene glycols and other containing 2 to 100 recurring units of ethylene oxide), linkers in the VLR system can be independently a chemical bond or the residue of a linking group. The phrase "residue of a linking group" as used herein refers to a moiety that remains, results, or is derived from the reaction of a vector reactive group with a reactive site on a vector. The phrase "vector reactive group" as used herein refers to any group which can react with functional groups typically found on vectors, the derivatization of which only minimally effects the ability of the vector to bind to its receptor. However, it is specifically contemplated that such vector reactive groups can also react with functional groups typically found on relevant protein molecules. Thus, in one aspect the linkers useful in the practice of this invention derive from those groups which can react with any relevant molecule which comprises a vector as described above containing a reactive group, whether or not such relevant molecule is a protein, to form a linking. group.

Preferred linking groups are derived from vector reactive groups selected from but not limited to:

a group that will react directly with carboxy, aldehyde, amine (NHR), alcohols, sulfhydryl groups, activated methylenes and the like, on the vector, for example, active halogen containing groups including, for example, chloromethylphenyl groups and chloroacetyl [ClCH$_2$C(=O)—] groups, activated 2-(leaving group substituted)-ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like.

A group that can react readily with modified vector molecules containing a vector reactive group, i.e., vectors containing a reactive group modified to contain reactive groups such as those mentioned in the tables above, for example, by oxidation of the vector to an aldehyde or a carboxylic acid, in which case the "linking group" can be derived from reactive groups selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of said linking groups can contain from 1 to about 20 carbon atoms. The aryl portions of said linking groups can contain from about 6 to about 20 carbon atoms; and a group that can be linked to the vector containing a reactive group, or to the modified vector as noted above by use of a crosslinking agent. The residues of certain useful crosslinking agents, such as, for example, homobifunctional and heterobifunctional gelatin hardeners, bisepoxides, and bisisocyanates can become a part of a linking group during the crosslinking reaction. Other useful crosslinking agents, however, can facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847 and the ethers of U.S. Pat. No. 4,877,724. With these crosslinking agents, one of the reactants such as the vector must have a carboxyl group and the other such as a long chain spacer must have a reactive amine, alcohol, or sulfhydryl group. In amide bond formation, the crosslinking agent first reacts selectively with the carboxyl group, then is split out during reaction of the thus "activated" carboxyl group with an amine to form an amide linkage between thus covalently bonding the two moieties.

An advantage of this approach is that crosslinking of like molecules, e.g., vector to vector is avoided, whereas the reaction of, for example, homo-bifunctional crosslinking agents is nonselective and unwanted crosslinked molecules are obtained.

Preferred useful linking groups are derived from various heterobifunctional cross-linking reagents such as those listed in the Pierce Chemical Company Immunotechnology Catalog—Protein Modification Section, (1995 and 1996). Useful non-limiting examples of such reagents include:

Sulfo-SMCC Sulfosuccinimidyl 4-(N-maleimidomethyl) cyclohexane-l-carboxylate.

Sulfo-SIAB Sulfosuccinimidyl (4-iodoacetyl) aminobenzoate.

Sulfo-SMPB Sulfosuccinimidyl 4-(p-maleimidophenyl) butyrate.

2-IT 2-Iminothiolane.

SATA N-Succinimidyl S-acetylthioacetate.

In addition to the foregoing description, the linking groups, in whole or in part, can also be comprised of and derived from complementary sequences of nucleotides and residues of nucleotides, both naturally occurring and modified, preferably non-self-associating oligonucleotide sequences. Particularly useful, non-limiting reagents for incorporation of modified nucleotide moieties containing reactive functional groups, such as amine and sulfhydryl groups, into an oligonucleotide sequence are commercially available from, for example, Clontech Laboratories Inc. (Palo Alto Calif.) and include Uni-Link AminoModifier (Catalog #5190), Biotin-ON phosphoramidite (Catalog #5191), N-MNT-C6-AminoModifier (Catalog #5202), AminoModifier II (Catalog #5203), DMT-C6-3'Amine-ON (Catalog #5222), C6-ThiolModifier (Catalog #5211), and the like. In one aspect, linking groups of this invention are derived from the reaction of a reactive functional group such as an amine or sulfhydryl group as are available in the above Clontech reagents, one or more of which has been incorporated into an oligonucleotide sequence, with, for example, one or more of the previously described vector reactive groups such as a heterobifunctional group on the vector.

By attaching two complementary oligonucleotide sequences one to the vector and the other to the reporter the resulting double-stranded hybridized oligonucleotide then comprises the linking group between the vector and reporter.

Other polymer systems that serve as linkers include:

Poly(L or D or DL-amino acids)=proteins and peptides; naturally occuring or synthetic Pseudo Poly(amino acids)=(amino acids linked by non-amide bonds)

Poly (L or D or DL-lactide) and the co-polymers e.g

Poly (L-lactide/DL-lactide)Poly (glycolide)

L-lactide/glycolide co-polymers

Poly-caprolactone and its co-polymers

Polyanhydrides

Poly (ortho esters)

Polyphosphazenes

Long-chain straight or branched lipids (& phospholipids)

Sugars and carbohydrates

Oligonucleotides (see above)

as well as mixtures of the above.

Linking agents used in accordance with the invention will in general bring about linking of vector to reporter or reporter to reporter with some degree of specificity, and may also be used to attach one or more therapeutically active agents.

The present invention accordingly provides a tool for therapeutic drug delivery in combination with vector-mediated direction of the product to the desired site. By "therapeutic" or "drug" is meant an agent having a beneficial effect on a specific disease in a living human or non-human animal.

Therapeutic compounds used in accordance with the present invention may be encapsulated in-the interior. of a molecular aggregate or particulate linker or attached to or incorporated in the encapsulating walls of a vesicular linker. Thus, the therapeutic compound may be linked to a part of the surface, for example through covalent or ionic bonds, or may be physically mixed into an encapsulating material, particularly if the drug has similar polarity or solubility to the material, so as to prevent it from leaking out of the product before it is intended to act in the body. The release of the drug may be initiated merely by wetting contact with blood following administration or as a consequence of other internal or external influences, e.g. dissolution processes catalyzed by enzymes or the use of magnetic heating where the reporter is a magnetic particle.

The therapeutic substance may be covalently linked to the encapsulating membrane surface of a vesicular linker using a suitable linking agent, e.g. as described herein. Thus, for example, one may initially prepare a phospholipid derivative to which the drug is bonded through a biodegradable bond or linker, and then incorporate this derivative into the material used to prepare the vesicle membrane, as described above. Alternatively, the agent may initially be prepared without the therapeutic, which may then be coupled to or coated onto particulate (eg. vesicular) agents prior to use. Thus, for example, a therapeutic could be added to a suspension of liposomes in aqueous media and shaken in order to attach or adhere the therapeutic to the liposomes.

The therapeutic may for example be a drug or prodrug known for use in combatting angiogenesis or tumors.

By targeting an agent according to the invention containing a prodrug-activating enzyme to areas of pathology one may image targeting of the enzyme, making it possible to visualise when the agent is targeted properly and when the agent has disappeared from non-target areas. In this way one can determine the optimal time for injection of prodrug into individual patients.

Another alternative is to incorporate a prodrug, a prodrug-activating enzyme and a vector in the same particulate linker reporter in such a way that the prodrug will only be activated after some external stimulus. Such a stimulus may, for example, be light stimulation of a chromophoric reporter, or magnetic heating of a superparamagnetic reporter after the desired targeting has been achieved.

So-called prodrugs may also be used in agents according to the invention. Thus drugs may be derivatised to alter their physicochemical properties and to adapt agent of the invention; such derivatised drugs may be regarded as prodrugs and are usually inactive until cleavage of the derivatising group regenerates the active form of the drug.

Therapeutics may easily be delivered in accordance with the invention to sites of angiogenesis.

By way of example, where the reporter is a chelated metal species (eg. a paramagnetic metal ion or a metal radionuclide), the linker may comprise a chain attached to a metal chelating group, a polymeric chain with a plurality of metal chelating groups pendant from the molecular backbone or incorporated in the molecular backbone, a branched polymer with metal chelating groups at branch termini (eg. a dendrimeric polychelant), etc. What is required of the linker is simply that it bind the vector and reporter moieties together for an adequate period. By adequate period is meant a period sufficient for the contrast agent to exert its desired effects, eg. to enhance contrast in vivo during a diagnostic imaging procedure.

Thus, in certain circumstances, it may be desirable that the linker biodegrade after administration. By selecting an appropriately biodegradable linker it is possible to modify the biodistribution and bioelimination patterns for the vector and/or reporter. Where vector and/or reporter are biologically active or are capable of exerting undesired effects if retained after the imaging procedure is over, it may be desirable to design in linker biodegradability which ensures appropriate bioelimination or metabolic breakdown of the vector and/or reporter moieties. Thus a linker may contain a biodegradable function which on breakdown yields breakdown products with modified biodistribution patterns which result from the release of the reporter from the vector or from fragmentation of a macromolecular structure. By way of example for linkers which carry chelated metal ion reporters it is possible to have the linker incorporate a biodegradable function which on breakdown releases an excretable chelate compound containing the reporter. Accordingly, biodegradable functions may if desired be incorporated within the linker structure, preferably at sites which are (a) branching sites, (b) at or near attachment sites for vectors or reporters, or (c) such that biodegradation yields physiologically tolerable or rapidly excretable fragments.

Examples of suitable biodegradable functions include ester, amide, double ester, phosphoester, ether, thioether, guanidyl, acetal and ketal functions.

As discussed above, the linker group may if desired have built into its molecular backbone groups which affect the biodistribution of the contrast agent or which ensure appropriate spatial conformation for the contrast agent, eg. to allow water access to chelated paramagnetic metal ion reporters. By way of example the linker backbone may consist in part or essentially totally of one or more poly-alkylene oxide chains.

Thus the linker may be viewed as being a composite of optionally biodegradable vector binding ($V_b$) and reporter binding ($R_b$) groups joined via linker backbone ($L_b$) groups, which linker backbone groups may carry linker side chain ($L_{sc}$) groups to modify biodistribution etc. and may themselves incorporate biodegradable functions. The $R_b$ and $V_b$ binding groups may be pendant from the linker backbone or may be at linker backbone termini, for example with one $R_b$ or $V_b$ group at one $L_b$ terminus, with $R_b$ or $V_b$ groups linking together two $L_b$ termini or with one $L_b$ terminus carrying two or more $R_b$ or $V_b$ groups. The $L_b$ and $L_{sc}$ groups will conveniently be oligomeric or polymeric structures (eg. polyesters, polyamides, polyethers, polyamines, oligopeptides, polypeptides, oligo and polysaccharides, oligonucleotides, etc.), preferably structures having at least in part a hydrophilic or lipophilic nature, eg. hydrophilic, amphiphilic or lipophilic structures.

The linker may be low, medium or high molecular weight, eg. up to 2MD. Generally higher molecular weight linkers will be preferred if they are to be loaded with a multiplicity of vectors or reporters or if it is necessary to space vector and reporter apart, or if the linker is itself to serve a role in the modification of biodistribution. In general however linkers will be from 100 to 100 000 D, especially 120 D to 20 kD in molecular weight.

Conjugation of linker to vector and linker to reporter may be by any appropriate chemical conjugation technique, eg. covalent bonding (for example ester or amide formation), metal chelation or other metal coordinative or ionic bonding, again as described above.

Examples of suitable linker systems include the magnifier polychelant structures of U.S. Pat. No. 5,364,613 and PCT/EP90/00565, polyaminoacids (eg. polylysine), functionalised PEG, polysaccharides, glycosaminoglycans, dendritic polymers such as described in WO93/06868 and by Tomalia et al. in Angew. Chem. Int. Ed. Engl. 29:138–175 (1990), PEG-chelant polymers such as described in W94/08629, WO94/09056 and WO96/26754, etc.

Where the reporter is a chelated metal ion, the linker group will generally incorporate the chelant moiety. Alternatively, the chelated metal may be carried on or in a particulate reporter. In either case, conventional metal chelating groups such as are well known in the fields of radiopharmaceuticals and MRI contrast media may be used, eg. linear, cyclic and branched polyamino-polycarboxylic acids and phosphorus oxyacid equivalents, and other sulphur and/or nitrogen ligands known in the art, eg. DTPA, DTPA-BMA, EDTA, D03A, TMT (see for example U.S. Pat. No. 5,367,080), BAT and analogs (see for example Ohmono et al., J. Med. Chem. 35: 157–162 (1992) and Kung et al. J. Nucl. Med. 25: 326–332 (1984)), the $N_2S_2$ chelant ECD of Neurolite, MAG (see Jurisson et al. Chem. Rev. 93: 1137–1156 (1993)), HIDA, DOXA (1-oxa-4,7,10-triazacyclododecanetriacetic acid), NOTA (1,4,7-triazacyclononanetriacetic acid), $TET_A$ (1,4,8,11-tetraazacyclotetradecanetetraacetic. acid), THT 4'-(3-amino-4-methoxy-phenyl)-6,6"-bis(N',N'-dicarboxymethyl-N-methylhydrazino)-2,2':6',2"-terpyridine), etc. In this regard, the reader is referred to the patent literature of Sterling Winthrop, Nycomed (including Nycomed Imaging and Nycomed Salutar), Schering, Mallinckrodt, Bracco and Squibb relating to chelating agents for diagnostic metals, eg. in MR, X-ray and radiodiagnostic agents. See for example U.S. Pat. No. 4,647,447, EP-A-71564, U.S. Pat. No. 4,687,659, WO89/00557, U.S. Pat. No. 4,885,363, and EP-A-232751.

Reporter

The reporter moieties in the contrast agents of the invention may be any moiety capable of detection either directly or indirectly in an in vivo diagnostic imaging procedure, eg. moieties which emit or may be caused to emit detectable radiation (eg. by radioactive decay, fluorescence excitation, spin resonance excitation, etc.), moieties which affect local electromagnetic fields (eg. paramagnetic, superparamagnetic, ferrimagnetic or ferromagnetic species), moieties which absorb or scatter radiation energy (eg. chromophores and fluorophores), particles (including liquid containing vesicles), heavy elements and compounds thereof, and moieties which generate a detectable substance, etc.

A very wide range of materials detectable by diagnostic imaging modalities is known from the art and the reporter will be selected according to the imaging modality to be used. Thus for example for ultrasound imaging an echogenic material; or a material capable of generating an echogenic material will normally be selected, for X-ray imaging the reporter will generally be or contain-a heavy atom (eg. of atomic weight 38 or above), for MR imaging the reporter will either be a non zero nuclear spin isotope (such as $^{19}F$) or a material having unpaired electron spins and hence paramagnetic, superparamagnetic, ferrimagnetic or ferromagnetic properties, for light imaging the reporter will be a light scatterer (eg. a coloured or uncoloured particle), a light absorber or a light emitter, for magnetometric imaging the reporter will have detectable magnetic properties, for electrical impedance imaging the reporter will affect electrical impedance and for scintigraphy, SPECT, PET etc. the reporter will be a radionuclide.

Examples of suitable reporters are widely known from the diagnostic imaging literature, eg. magnetic iron oxide particles, X-ray contrast agent containing vesicles, chelated paramagnetic metals (such as Gd, Dy, Mn, Fe etc.). See for example U.S. Pat. No. 4,647,447, PCT/GB97/00067, U.S. Pat. No. 4,863,715, U.S. Pat. No. 4,770,183, WO96/09840, WO85/02772, WO92/17212, PCT/GB97/00459, EP-A-554213, U.S. Pat. No. 5,228,446, WO91/15243, WO93/05818, WO96/23524, WO96/17628, U.S. Pat. No. 5,387,080, WO95/26205, GB9624918.0, etc.

Particularly preferred as reporters are: chelated paramagnetic metal ions such as Gd, Dy, Fe, and Mn, especially when chelated by macrocyclic chelant groups (eg. tetraazacyclododecane chelants such as DOTA, DO3A, HP-DO3A and analogues thereof) or by linker chelant groups such as DTPA, DTPA-BMA, EDTA, DPDP, etc; metal radionuclide such as $^{90}Y$, $^{99m}Tc$, "$^{111}In$, $^{47}Sc$, $^{67}/Ga$, $^{51}Cr$, $^{117m}Sn$, $^{67}Cu$, $^{167}Tm$, $^{97}Ru$, $^{188}Re$, $^{117}Lu$, $^{199}Au$, $^{203}Pb$ and $^{141}Ce$; superparamagnetic iron oxide crystals; chromophores and fluorophores having absorption and/or emission maxima in the range 300–1400 nm, especially 600 nm to 1200 nm, in particular 650 to 1000 nm; chelated heavy metal cluster ions (eg. W or Mo polyoxoanions or the sulphur or mixed oxygen/sulphur analogs); covalently bonded non-metal atoms which are either high atomic number (eg. iodine) or are radioactive, eg $^{123}I$, $^{131}I$, etc. atoms; iodinated compound containing vesicles; etc.

Stated generally, the reporter may be (1) a chelatable metal or polyatomic metal-containing ion (ie. TcO, etc), where the metal is a high atomic number metal (eg. atomic number greater than 37), a paramagentic species (eg. a transition metal or lanthanide), or a radioactive isotope, (2) a covalently bound non-metal species which is an unpaired electron site (eg. an oxygen or carbon in a persistant free radical), a high atomic number non-metal, or a radioisotope, (3) a polyatomic cluster or crystal containing high atomic number atoms, displaying cooperative magnetic behaviour (eg. superparamagnetism, ferrimagnetism or ferromagnetism) or containing radionuclides, (4) a chromophore (by which term species which are fluorescent or phosphorescent are included), eg. an inorganic or organic structure, particularly a complexed metal ion or an organic group having an extensive delocalized electron system, or (5) a structure or group having electrical impedance varying characteristics, eg. by virtue of an extensive delocalized electron system.

Examples of particular preferred reporter groups are described in more detail below.

Chelated metal reporters: metal radionuclides. paramacnetic metal ions, fluorescent metal ions, heavy metal ions and cluster ions.

Preferred metal radionuclides include $^{90}Y$, $^{99m}Tc$, $^{111}In$, $^{47}Sc$, $^{67}Ga$, $^{51}Cr$, $^{177m}Sn$, $^{67}Cu$, $^{179}Tm$, $^{97}Ru$, $^{188}Re$, $^{177}Lu$, 199Au, $^{203}Pb$ and $^{141}Ce$.

Preferred paramagnetic metal ions include ions of transition and lanthanide metals (eg. metals having atomic numbers of 6 to 9, 21–29, 42, 43, 44, or 57–71), in particular ions of Cr, V, Mn, Fe, Co, Ni, Cu, La, Ce, Pr, Nd, Pm, Sm, Eu, Gd, Tb, Dy, Ho, Er, Tm, Yb and Lu, especially of Mn, Cr, Fe, Gd and Dy, more especially Gd.

Preferred fluorescent metal ions include lanthanides, in particular La, Ce, Pr, Nd, Pm, Sm, Eu, Gd, Tb, Dy, Ho, Er, Tm, Yb, and Lu. Eu is especially preferred.

Preferred heavy metal-containing reporters may include atoms of Mo, Bi, Si, and W, and in particular may be polyatomic cluster ions (eg. Bi compounds and W and Mo oxides) as described in WO91/14460, WO92/17215, WO96/40287, and WO96/22914.

The metal ions are desirably chelated by chelant groups on the linker moiety or in or on a particle, (eg. a vesicle or a porous or non-porous inorganic or organic solid), in particular linear, macrocyclic, terpyridine and $N_2S_2$ chelants, such as for example DTPA, DTPA-BMA, EDTA, DO3A, TMT. Further examples of suitable chelant groups are disclosed in U.S. Pat. No. 4,647,447, WO89/00557, U.S. Pat. No. 5,367,080, U.S. Pat. No. 5,364,613, etc.

The linker moiety or the particle may contain one or more such chelant groups, if desired metallated by more than one metal species (eg. so as to provide reporters detectable in different imaging modalities).

Particularly where the metal is non-radioactive, it is preferred that a polychelant linker or particulate reporter be used.

A chelant or chelating group as referred to herein may comprise the residue of one or more of a wide variety of chelating agents that can complex a metal ion or a polyatomic ion (eg. TCO).

As is well known, a chelating agent is a compound containing donor atoms that can combine by coordinate bonding with a metal atom to form a cyclic structure called a chelation complex or chelate. This class of compounds is described in the Kirk-Othmer Encyclopedia of Chemical Technology, Vol. 5, 339–368.

The residue of a suitable chelating agent can be selected from polyphosphates, such as sodium tripolyphosphate and hexametaphosphoric acid; aminocarboxylic acids, such as ethylenediaminetetraacetic acid, N-(2-hydroxy)ethylene-diaminetriacetic acid, nitrilotriacetic acid, N,N-di(2-hydroxyethyl)glycine, ethylenebis(hydroxyphenylglycine) and diethylenetriamine pentacetic acid; 1,3-diketones, such as acetylacetone, trifluoroacetylacetone, and thenoyltrifluoroacetone; hydroxycarboxylic acids, such as tartaric acid, citric acid, gluconic acid, and 5-sulfosalicyclic acid; polyamines, such as ethylenediamine, diethylenetriamine, triethylenetetraamine, and triaminotriethylamine; aminoalcohols, such as triethanolamine and N-(2-hydroxyethyl)ethylenediamine; aromatic heterocyclic bases, such as 2,2'-diimidazole, picoline amine, dipicoline amine and 1,10-phenanthroline; phenols, such as salicylaldehyde, disulfopyrocatechol, and chromotropic acid; aminophenols, such as 8-hydroxyquinoline and oximesulfonic acid; oximes, such as dimethylglyoxime and salicylaldoxime; peptides containing proximal chelating-functionality such as polycysteine, polyhistidine, polyaspartic acid, polyglutamic acid, or combinations of such amino acids; Schiff bases, such as disalicylaldehyde 1,2-propylenediimine; tetrapyrroles, such as tetraphenylporphin and phthalocyanine; sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea; synthetic macrocyclic compounds, such as dibenzo[18]crown-6, $(CH_3)_6$-[14]-4,11]-diene-$N_4$, and (2.2.2-cryptate); phosphonic acids, such as nitrilotrimethylene-phosphonic acid, ethylenediaminetetra (methylenephosphonic acid), and hydroxyethylidenediphosphonic acid, or combinations of two or more of the above agents. The residue of a suitable chelating agent preferably comprises a polycarboxylic acid group and preferred examples include: ethylenediamine-N,N,N',N'-tetraacetic acid (EDTA); N,N,N',N'',N''-diethylene-triaminepentaacetic acid (DTPA); 1,4,7,10-tetraazacyclododecane-N,N',N'',N'''tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); trans (1,2)-cyclohexanodiethylene-triamine-pentaacetic acid (CDTPA).

Other suitable residues of chelating agents comprise proteins modified for the chelation of metals such as technetium and rhenium as described in U.S. Pat. No. 5,078,985, the disclosure of which is hereby incorporated by reference.

Suitable residues of chelating agents may also derive from N3S and N2S2 containing compounds, as for example, those disclosed in U.S. Pat. Nos. 4,444,690; 4,670,545; 4,673,562; 4,897,255; 4,965,392; 4,980,147; 4,988,496; 5,021,556 and 5,075,099.

Other suitable residues of chelating are described in PCT/US91/08253, the disclosure of which is hereby. incorporated by reference.

Preferred chelating groups are selected from the group consisting of 2-amiomethylpyridine, iminoacetic acid, iminodiacetic acid, ethylenediaminetetraacetic acid (EDTA), diethylenetriaminepentaacetic acid (DTPA), 1,4,7,10-tetraazacyclododecane-1,4,7,10-tetraacetic acid (DOTA), carbonyliminodiacetic acid, methyleneiminoacetic acid, methyleneiminodiacetic acid, ethylenethioethylene-iminoacetic acid, ethylenethioethyleneiminodiacetic acid, TMT, a terpyridinyl group, a chelating agent comprising a terpyridyl group and a carboxymethylamino group, or a salt of any of the foregoing acids. Especially preferred chelating groups are DTPA, DTPA-BMA, DPDP, TMT, DOTA and HPDO3A.

Representative chelating groups are also described in U.S. Pat. No. 5,559,214 A, WO 9526754, WO 9408624, WO 9409056, WO 9429333, WO 9408624, WO 9408629 A1, WO 9413327 A1 and WO 9412216 A1.

Methods for metallating any chelating agents present are within the level of skill in the art. Metals can be-incorporated into a chelant moiety by any one of three general methods: direct incorporation, template synthesis and/or transmetallation. Direct incorporation is preferred.

Thus it is desirable that the metal ion be easily complexed to the chelating agent, for example, by merely exposing or mixing an aqueous solution of the chelating agent-containing moiety with a metal salt in an aqueous solution preferably having a pH in the range of about 4 to about 11. The salt can be any salt, but preferably the salt is a water soluble salt of the metal such as a halogen salt, and more preferably such salts are selected so as not to interfere with the binding of the metal ion with the chelating agent. The chelating agent-containing moiety is preferably in aqueous solution at a pH of between about 5 and about 9, more preferably between pH about 6 to about 8. The chelating agent-containing moiety can be mixed with buffer salts such as citrate, acetate, phosphate and borate to produce the optimum pH. Preferably, the buffer salts are selected so as not to interfere with the subsequent binding of the metal ion to the chelating agent.

In diagnostic imaging, the vector-linker-reporter (VLR) construct preferably contains a ratio of metal radionuclide ion to chelating agent that is,effective in such diagnostic imaging applications. In preferred embodiments, the mole ratio of metal ion per chelating agent is from about 1:1,000 to about 1:1.

In radiotherapeutic applications, the VLR preferably contains a ratio of metal radionuclide ion to chelating agent that is effective in such therapeutic applications. In preferred embodiments, the mole ratio of metal ion per chelating agent is from about 1:100 to about 1:1. The radionuclide can be selected, for example, from radioisotopes of Sc, Fe, Pb, Ga, Y, Bi, Mn, Cu, Cr, Zn, Ge, Mo, Ru, Sn, Sr, Sm, Lu, Sb, W, Re, Po, Ta and Tl. Preferred radionuclides include $^{44}$Sc, $^{64}$Cu, $^{67}$C, $^{212}$Pb, $^{68}$Ga, $^{90}$Y, $^{153}$Sm, $^{212}$Bi, $^{186}$Re and $^{188}$Re. Of these, especially preferred is $^{90}$Y. These radioisotopes can be atomic or preferably ionic.

The following isotopes or isotope pairs can be used for both imaging and therapy without having to change the radiolabeling methodology or chelator: $^{47}$Sc$_{21}$; $^{141}$Ce$_{58}$; $^{188}$Re$_{75}$; $^{177}$Lu$_{71}$; $^{199}$Au$_{79}$; $^{47}$Sc$_{21}$; $^{131}$I$_{53}$; $^{67}$Cu$_{29}$; $^{153}$I$_{53}$ and $^{123}$I$_{53}$; $^{188}$Re$_{75}$ and $^{99m}$Tc$_{43}$; $^{90}$Y$_{39}$ and $^{87}$Y$_{39}$; $^{47}$Sc$_{21}$ and $^{44}$Sc$_{21}$; $^{90}$Y$_{39}$ and $^{123}$I$_{53}$; $^{146}$Sm$_{62}$ and $^{153}$Sm$_{62}$; and $^{90}$Y$_{39}$ and $^{111}$In$_{49}$.

Where the linker moiety contains a single chelant, that chelant may be attached directly to the vector moiety, eg. via one of the metal coordinating groups of the chelant which may form an ester, amide, thioester or thioamide bond with an amine, thiol or hydroxyl group on the vector. Alternatively the vector and chelant may be directly linked via a functionality attached to the chelant backbone, eg. a CH$_2$-phenyl-NCS group attached to a ring carbon of DOTA as proposed by Meares et al. in JACS 110:6266–6267(1988), or indirectly via a homo or hetero-bifunctional linker, eg. a bis amine, bis epoxide, diol, diacid, difunctionalised PEG, etc. In that event, the bifunctional linker will conveniently provide a chain of 1 to 200, preferably 3 to 30 atoms between vector and chelant residue.

Where the linker moiety contains a plurality of chelant groups, the linker preferably is or contains portions of formula

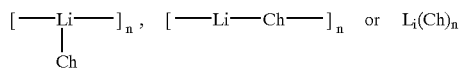

where Ch is a chelant moiety and Li is a linker backbone component, ie. the linker preferably has pendant chelants, in-backbone chelants or terminal chelants or a combination thereof. The pendant and in-backbone polymeric structures may be branched but more preferably are linear and the repeat units (LiCh) or other repeat units in the polymer may have in-backbone or pendant biodistribution modifying groups, eg. polyalkylene groups as in WO94/08629, WO94/09056, and WO96/20754. The terminal chelant structures Li(Ch)$_n$, which may be dendritic polymers as in WO93/06868, may have biodistribution modifying groups attached to termini not occupied by chelants and may have biodegradation enhancing sites within the linker structure as in WO95/28966.

The chelant moieties within the polychelant linker may be attached via backbone functionalization of the chelant or by utilization of one or more of the metal coordinating groups of the chelant or by amide or ether bond formation between acid chelant and an amine or hydroxyl carrying linker backbone, eg. as in polylysine-polyDTPA, polylysine-polyDOTA and in the so-called magnifier polychelants, of PCT/EP96/00565. Such polychelant linkers may be conjugated to one or more vector groups either directly (eg. utilizing amine, acid or hydroxyl groups in the polychelant linker) or via a bifunctional linker compound as discussed above for monochelant linkers.

Where the chelated species is carried by a particulate (or molecular aggregate, eg. vesicular) linker, the chelate may for example be an unattached mono or polychelate (such as Gd DTPA-BMA or Gd HP-DO3A) enclosed within the particle or it may be a mono or polychelate conjugated to the particle either by covalent bonding or by interaction of an anchor group (eg. a lipophilic group) on the mono/polychelate with the membrane of a vesicle (see for example PCT/GB95/02378).

Non-metal atomic reporters

Preferred non-metal atomic reporters include radioisotopes such as $^{123}$I and $^{131}$I as well as non zero nuclear spin atoms such as $^{19}$F, and heavy atoms such as I.

Such reporters, preferably a plurality thereof, eg. 2 to 200, may be covalently bonded to a linker backbone, either directly using conventional chemical synthesis techniques or via a supporting group, eg. a triiodophenyl group.

In an embodiment of this invention, the use of radioisotopes of iodine is specifically contemplated. For example, if the vector or linker is comprised of substituents that can be chemically substituted by iodine in a covalent bond forming reaction, such as, for example, substituents containing hydroxyphenyl functionality, such substituents can be labeled by methods well known in the art with a radioisotope of iodine. The iodine species can be used in therapeutic and diagnostic imaging applications. While, at the same time, a metal in a chelating agent on the same vector-linker can also be used in either therapeutic or diagnostic imaging applications. As with the metal chelants discussed above, such metal atomic reporters may be linked to the linker or carried in or on a particulate linker, eg. in a vesicle (see WO95/26205 and GB9624918.0).

Linkers of the type described above in connection with the metal reporters may be used for non-metal atomic reporters with the non-metal atomic reporter or groups carrying such reporters taking the place of some or all of the chelant groups.

Organic Chromophoric or Fluorophoric Reporters

Preferred organic chromophoric and fluorophoric reporters include groups having an extensive delocalized electron system, eg. cyanines, merocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes, etc. Examples of suitable organic or metallated organic chromophores may be found in "Topics in Applied Chemistry: Infrared absorbing dyes" Ed. M. Matsuoka, Plenum, N.Y. 1990, "Topics in Applied Chemistry: The Chemistry and Application of Dyes", Waring et al., Plenum, N.Y., 1990, "Handbook of Fluorescent Probes and Research Chemicals" Haugland, Molecular Probes Inc, 1996, DE-A-4445065, DE-A-4326466, JP-A-3/228046, Narayanan et al. J. Org. Chem. 60: 2391–2395 (1995), Lipowska et al. Heterocyclic Comm. 1: 427–430 (1995), Fabian et al. Chem. Rev. 92: 1197 (1992), WO96/23525, Strekowska et al. J. Org. Chem. 57: 4578–4580 (1992), WO (Axis) and WO96/17628. Particular examples of chromophores which may be used include xylene cyanole, fluorescein, dansyl, NBD, indocyanine green, DODCI, DTDCI, DOTCI and DDTCI.

Particularly preferred are groups which have absorption maxima between 600 and 1000 nm to avoid interference with haemoglobin absorption (eg. xylene cyanole).

Further such examples include:

cyanine dyes: such as heptamethinecyanine dyes, e.g. compounds 4a to 4g Table II on page 26 of Matsuoka (supra)

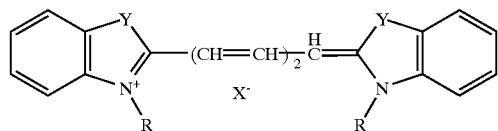

4a: where Y=S, X=I, R=Et
4b: where Y=S, X=ClO$_4$, R=Et
4c: where Y=Cme$_2$, X=I, R=Me
4d: where Y=CMe$_2$, X=ClO$_4$, R=Me
4e: where Y=CH=CH, X=I, R=Et
4f: where Y=CH=CH, X=Br, R=Et
4g: where Y=CH=CH, X=ClO$_4$, R=Et and in Table III on page 28 of Matsuoka (supra), i.e.

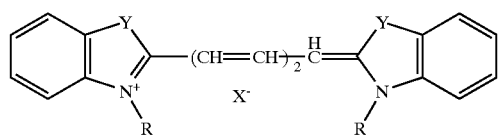

where Y=O, X=I, R=Me
where Y=CMe$_2$, X=I, R=Me
where Y=S, X=Br R=Et;

chalcogenopyrylomethine dyes, e.g., compounds 12 on page 31 of Matsuoka (supra), i.e.

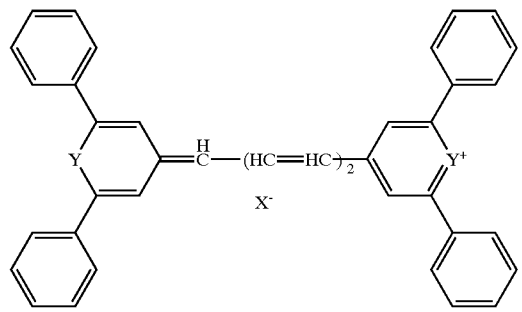

where Y=Te, Se, O or NR;

monochalcogenopyrylomethine dyes, e.g. compounds 13 on page 31, of Matsuoka (supra) i.e.

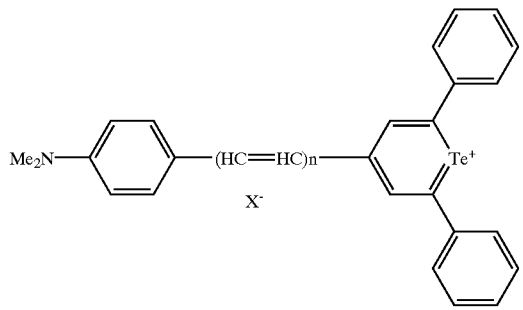

where n=1 or 2;

pyrilium dyes, e.g., compounds 14 (X=O) on page 32 of Matsuoka (supra), i.e.

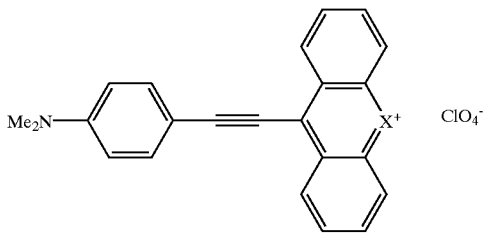

where X=O, S, or Se;

thiapyrilium dyes, e.g. compounds 15 on page 32, and compound I on page 167 of Matsuoka (supra), i.e.

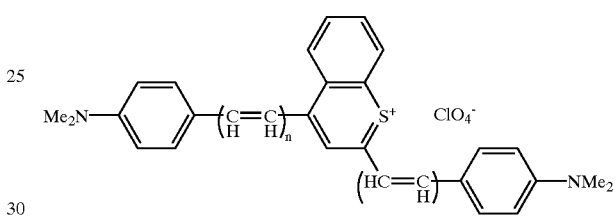

where n=1 or 2;

squarylium dyes, e.g. compound 10 and Table IV on page 30 of Matsuoka (supra), i.e.

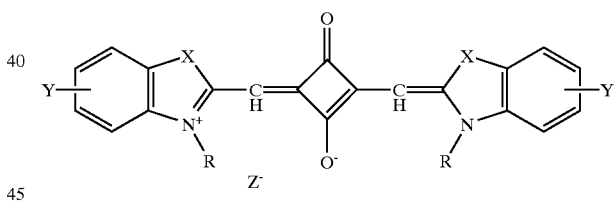

where X=CH=CH, Y=H, and R=Et,

X=S, Y=H, and R=Et, and

X=CMe$_2$, Y=H, and R=Me, and compound 6, page 26, of Matsuoka (supra), i.e.

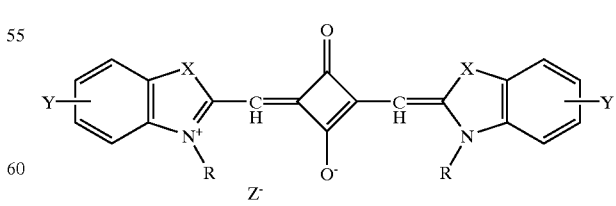

where X=CH=CH, Y H, and R=Et;

croconium dyes, e.g. compound 9 and Table IV on page 30 of Matusoka (supra), i.e.

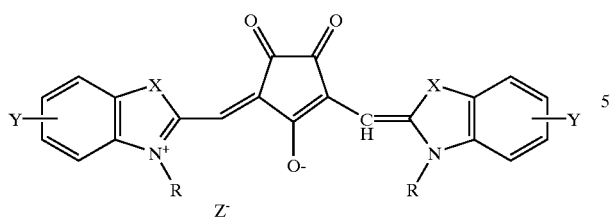

where X=CH=CH, Y=H, and R=Et,
X=S, Y=H, and R=Et,
X=CMe$_2$, Y=H, and R=Me,
and compound 7, page 26, of Matsuoka (supra), i.e.

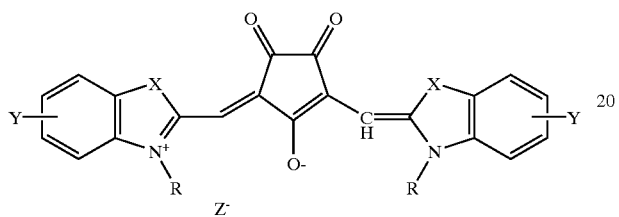

where X=CH=CH, Y=H, and R=Et;
azulenium dyes, e.g. compound 8 on page 27 of Matsuoka (supra), i.e.

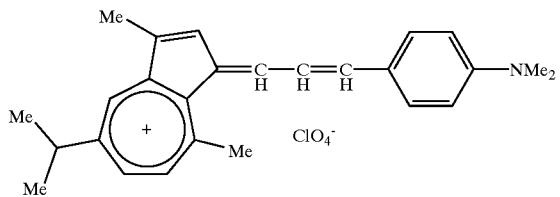

merocyanine dyes, e.g. compound 16, R=Me, on page 32 of Matsuoka (supra), i.e.

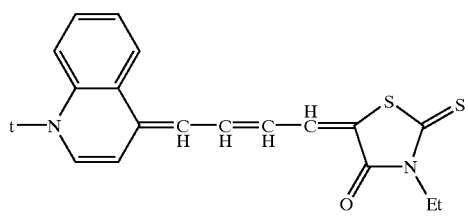

indoaniline dyes such as copper and nickel complexes of indoaniline dyes, e.g. compound 6 on page 63 of Matsuoka (supra), i.e.

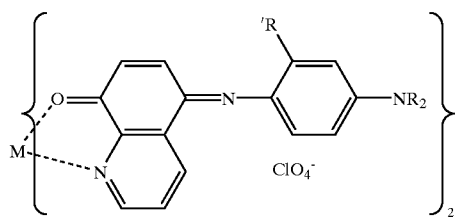

where R=Et, R'=Me, M=Cu,
R=Et, R'=Me, M=Ni,
R=Me, R'=H, M Cu, or
R=Me, R'=H, M=Ni,
benzo [a] phenoxazinium dyes and benzo [a] phenothiazinium dyes, e.g. as shown on page 201 of Matusoka (supra), i.e.

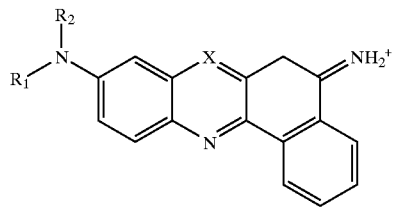

where X=O or S;
1,4-diaminoanthraquinone(N-alkyl)-3'-thioxo-2,3-dicarboximides, e.g. compound 20, on page 41 of Matusoka (supra)

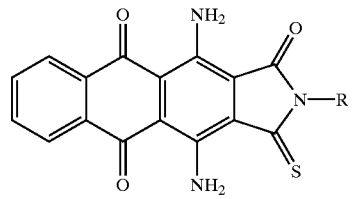

indanthrene pigments, e.g.

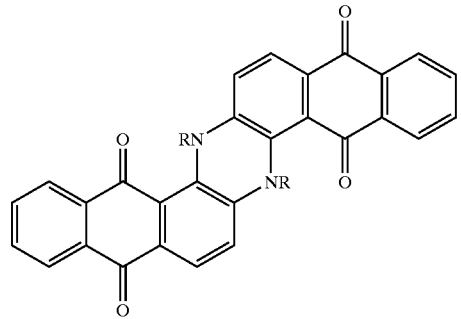

see compound 21 on page 41 of Matsuoka (supra);
2-arylamino-3,4-phthaloylacridone dyes, e.g. compound 22 on page 41 of Matsuoka (supra)

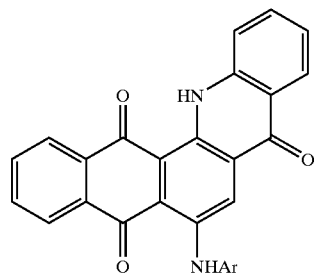

triphenoquinone dyes, e.g. compound 23 on page 41 of Matsuoka (supra)

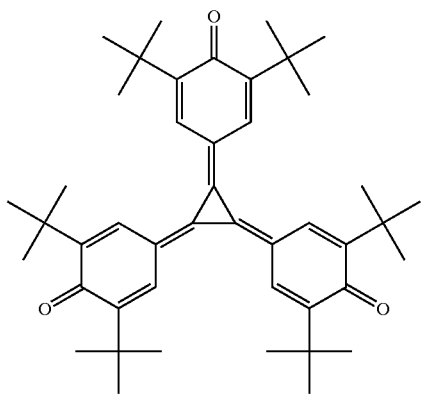

azo dyes, e.g. the monoazo dye, compound 2 on page 90 of Matsuoka (supra), i.e.

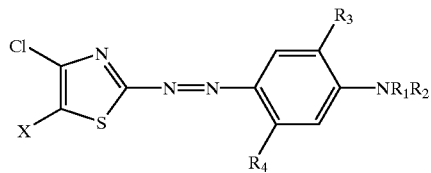

where X=CH═C(CN)$_2$, R$_1$=R$_2$=Et, R$_3$=R$_4$=H,
x=C(CN)═C(CN)$_2$, R$_1$=R$_2$=Et, R$_3$=R$_4$=H, or
X=

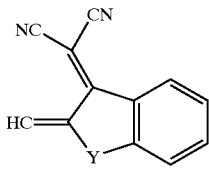

and Y=C═O, R$_1$=R$_2$=Et, R$_3$=R$_4$=H,
or Y=SO$_2$, R$_1$=H, R$_2$=CH(Me)nBu, R$_3$=OMe, and R$_4$=NHAc;

azo dyes, e.g. the polyazo dye, compound 5 on page 91 of Matsuoka (supra), i.e.

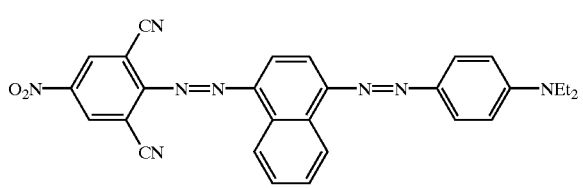

intramolecular charge transfer donor-acceptor infrared dyes, e.g. compounds 6 and 7 on page 91 of Matsuoka (supra), i.e.

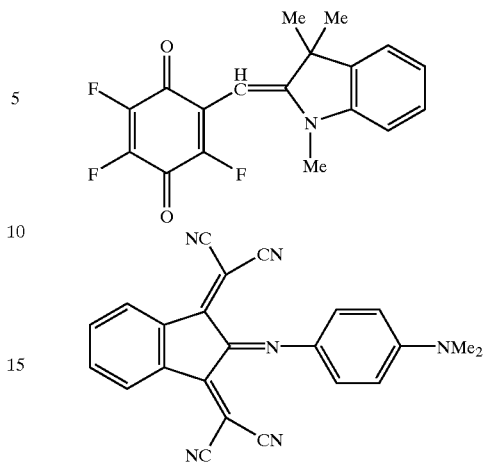

nonbenzenoid aromatic dyes, e.g. compound 8, a tropone, on page 92, of Matsuoka (supra), i.e.

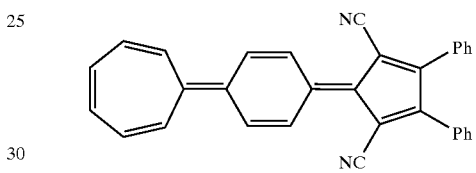

tetrazine radical dyes, e.g. compound 9 on page 92 of Matsuoka (supra), i.e.

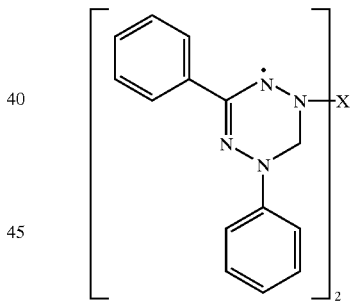

in which, X=p-phenylene or
X=p-terphenylene as well as compound 10 on page 92 of Matsuoka (supra), i.e.

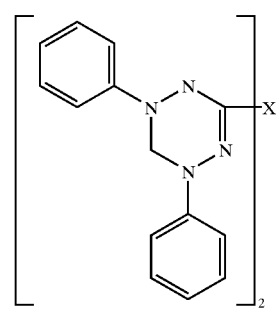

in which X=p-biphenyl;

cationic salts of tetrazine radical dyes, e.g. compound 11 on page 92 of Matsuoka (supra)

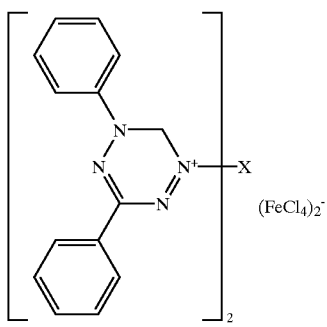

in which X=p-phenylene;

donor-acceptor intermolecular charge transfer dyes, e.g. CT complexes of compounds 13b and 14a to 14c on page 93 of Matsuoka (supra), i.e.

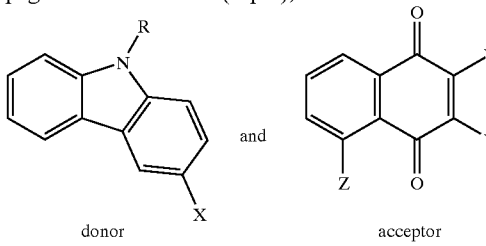

where X=CH=N—N(Ph)$_2$ in the donor and
a) Y=CN, Z=NO$_2$
b) Y=CN, Z=H or
a) Y=Cl, Z=NO$_2$ in the acceptor;

anthraquinone dyes, e.g. compounds 12 (X=S or Se) on page 38 of Matsuoka (supra), i.e.

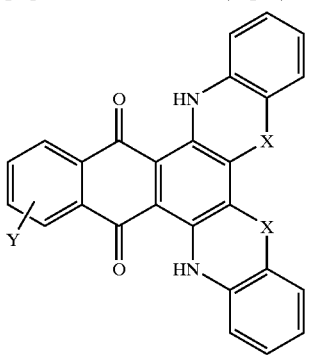

wherein X=S or Se and Y=tetrachloro, tetrabromo, 2,3-dicarboxylic acid, 2,3-dicarboxylic anhydride, or 2,3-dicarboxylic acid N-phenyl imide;

naphthoquinone dyes, e.g. compounds 2, 3, and 4 on page 37, of Matsuoka (supra), i.e.

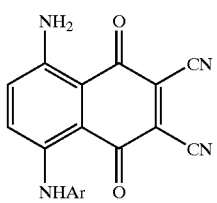

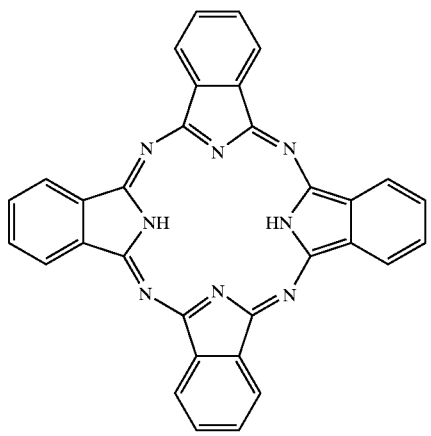

metallated azo dyes such as azo dyes containing nickel, cobalt, copper, iron, and manganese;

phthalocyanine dyes, e.g. compound 1 in Table II on page 51 of Matsuoka (supra), e.g.

naphthalocyanine dyes, e.g. compound 3 in Table II on page 51 of Matsuoka (supra), e.g.

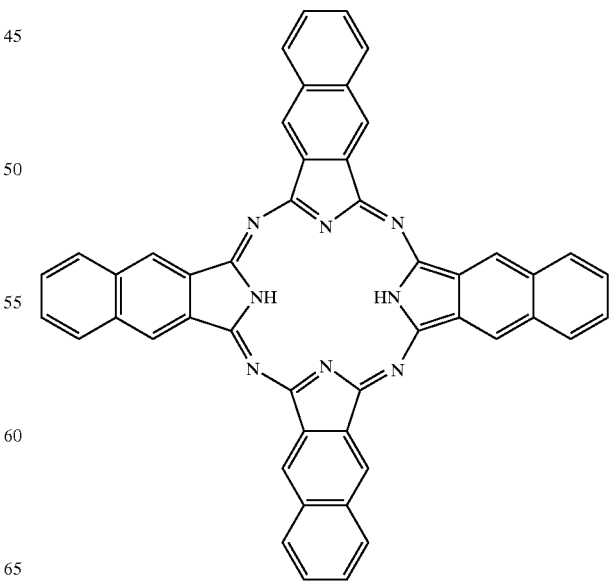

metal phthalocyanines such as phthalocyanines containing aluminum, silicon, nickel, zinc, lead, cadmium, magnesium, vanadium, cobalt, copper, and iron, e.g. compound 1 in Table III on page 52 of Matsuoka (supra), e.g.

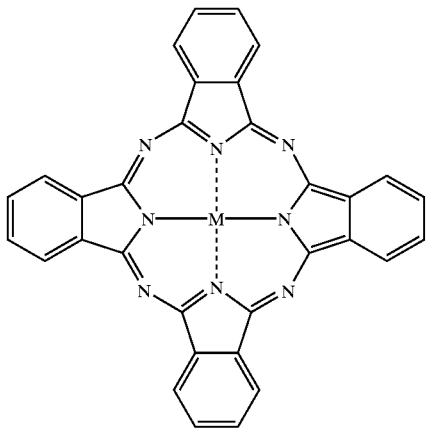

in which, for example, M=Mg;

metal naphthalocyanines such as naphthalocyanines containing aluminum, zinc, cobalt, magnesium, cadmium, silicon, nickel, vanadium, lead, copper, and iron, see compound 3 in Table III on page 52 of Matsuoka (supra), e.g.

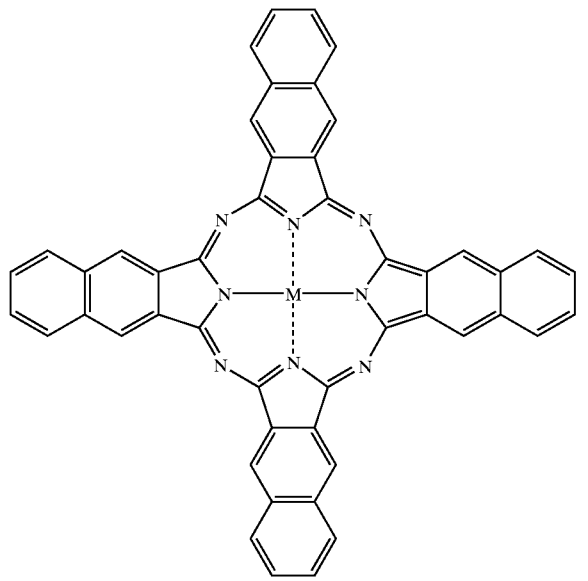

in which, for example, M=Mg;

bis(dithiolene) metal complexes comprising a metal ion such as nickel, cobalt, copper, and iron coordinated to four sulfur atoms in a bis(S,S'-bidentate) ligand complex, e.g. see Table I on page 59 of Matsuoka (supra)

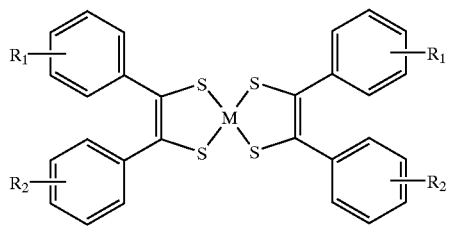

where $R_1=R_2=CF_3$, M=Ni, $R_1=R_2=$phenyl, M=Pd, $R_1=R_2=$phenyl, M=Pt, $R_1=$C4 to C10 alkyl, $R_2=$H, M=Ni, $R_1=$C4 to C10 alkyl, $R_2=$H, M=Pd, $R_1=$C4 to C10 alkyl, $R_2=$H, M=Pt, $R_1=R_2=$phenyl, M=Ni, $R_1=R_2=$p-$CH_3$-phenyl, M=Ni, $R_1=R_2=$p-$CH_3O$-phenyl, M=Ni, $R_1=R_2=$p-Cl-phenyl, M=Ni, $R_1=R_2=$p-$CF_3$-phenyl, M=Ni, $R_1=R_2=$3,4,-diCl-phenyl, M=Ni, $R_1=R_2=$o-Cl-phenyl, M=Ni, $R_1=R_2=$o-Br-phenyl, M=Ni, $R_1=R_2=$3,4,-diCl-phenyl, M=Ni, $R_1=R_2=$p-$CH_3$, M=Ni, $R_1=R_2=$2-thienyl, M=Ni, $R_1=$p-$(CH_3)_2$ N-phenyl, $R_2=$phenyl, M=Ni, and $R_1=$p-$(CH_3)_2$ N-phenyl, $R_2=$p-$H_2$N-phenyl, M=Ni;

bis(benzenedithiolate) metal complexes comprising a metal ion such as nickel, cobalt, copper, and iron coordinated to four sulfur atoms in a ligand complex, e.g. see Table III on page 62 of Matsuoka (supra), i.e.

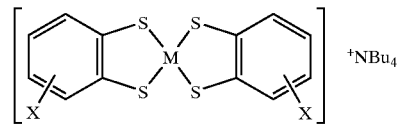

where

X=tetramethyl, M=Ni,

X=4,5-dimethyl, M=Ni,

X=4-methyl, M=Ni,

X=tetrachloro, M=Ni,

X=H, M=Ni,

X=4-methyl, M=Co,

X=4-methyl, M=Cu, and

X=4-methyl, M=Fe;

N,O-bidentate indoaniline dyes comprising a metal ion such as nickel, cobalt, copper, and iron coordinated to two nitrogen and two oxygen atoms of two N,O-bidentate indoaniline ligands, e.g. compound 6 in Table IV on page 63 of Matsuoka (supra), e.g.

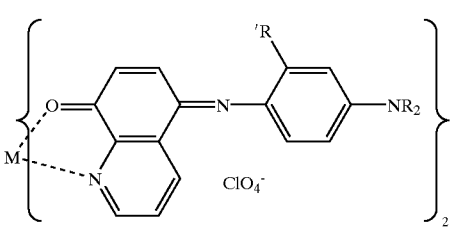

where R=Et, R'=Me, M=Cu,
R=Et, R'=Me, M=Ni,
R=Me, R'=H, M=Cu, and
R=Me, R'=H, M=Ni,
bis(S,O-dithiolene) metal complexes comprising a metal ion such as nickel, cobalt, copper, and iron coordinated to two sulfur atoms and two oxygen atoms in a bis(S, O-bidentate) ligand complex, e.g. see U.S. Pat. No. 3,806,46.2, e.g.

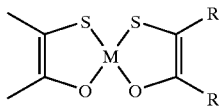

a-diimine-dithiolene complexes comprising a metal ion such as nickel, cobalt, copper, and iron coordinated to two sulfur atoms and two imino-nitrogen atoms in a mixed S,S— and N,N-bidentate diligand complex, e.g. see Table II on page 180, second from bottom, of Matsuoka (supra) (also see Japanese patents: 62/39, 682, 63/126,889 and 63/ 139,303), e.g.

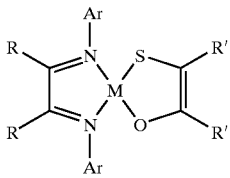

and tris(a-diimine) complexes comprising a metal ion coordinated to six nitrogen atoms in a triligand complex, e.g. see Table II on page 180 of Matsuoka (supra), last compound, (also see Japanese Patents 61/20,002 and 61/73,902), e.g.

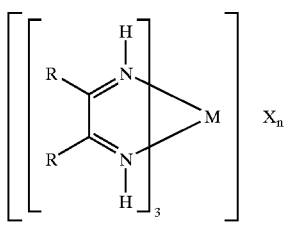

Representative examples of visible dyes include fluorescein derivatives, rhodamine derivatives, coumarins, azo dyes, metalizable dyes, anthraquinone dyes, benzodifuranone dyes, polycyclic aromatic carbonyl dyes, indigoid dyes, polymethine dyes, azacarbocyanine dyes, hemicyanine dyes, barbituates, diazahemicyanine dyes, stryrl dyes, diaryl carbonium dyes, triaryl carbonium dyes, phthalocyanine dyes, quinophthalone dyes, triphenodioxazine dyes, formazan dyes, phenothiazine. dyes such as methylene blue, azure A, azure B, and azure C, oxazine dyes, thiazine dyes, naphtholactam dyes, diazahemicyanine dyes, azopyridone dyes, azobenzene dyes, mordant dyes, acid dyes, basic dyes, metallized and premetahlized dyes, xanthene dyes, direct dyes, leuco dyes which can be oxidized to produce dyes with hues bathochromically shifted from those of the precursor leuco dyes, and other dyes such as those listed by Waring, D. R. and.Hallas, G., in "The Chemistry and Application of Dyes", Topics in Applied Chemistry, Plenum Press, New York, N.Y., 1990. Additonal dyes can be found listed in Haugland, R. P., "Handbook of Fluorescent Probes and Research Chemicals", Sixth Edition, Molecular Probes, Inc., Eugene Oreg., 1996.

Such chormophores and fluorophores may be covalently linked either directly to the vector or to or within a linker structure. Once again linkers of the type described above in connection with the metal reporters may be used for organic chromophores or fluorophores with the chromophores/fluorophores taking the place of some or all of the chelant groups.

As with the metal chelants discussed above chromophores/fluorophores may be carried in or on a particulate linker-moieties, eg. in or on a vesicle or covalently bonded to inert matrix particles that can also function as a light scattering reporter.

Particulate Reporters or Linker-Reporters

The particulate reporters and linker-reporters generally fall into two categories—those where the particle comprises a matrix or shell which carries or contains the reporter and those where the particle matrix is itself the reporter. Examples of the first category are: vesicles (eg. micelles and liposomes) containing a liquid or solid phase which contains the contrast effective reporter, eg. a chelated paramagnetic metal or radionuclide, or a water-soluble iodinated X-ray contrast agent; porous particles loaded with the reporter, eg. paramagnetic metal loaded molecular sieve particles; and solid particles, eg. of an inert biotolerable polymer, onto which the reporter is bound or coated, eg. dye-loaded polymer particles.

Examples of the second category are: light scattering organic or inorganic particles; magnetic particles (ie. superparamagnetic, ferromagnetic or ferrimagnetic particles); and dye particles.

Preferred particulate reporters or reporter-linkers include superparamagnetic particles (see U.S. Pat. No. 4,770,183, PCT/GB97/00067, WO96/09840, etc.), echogenic vesicles (see WO92/17212, PCT/GB97/00459, etc.), iodine-containing vesicles (see WO95/26205 and GB9624918.0), and dye-loaded polymer particles (see WO96/23524).

The particulate reporters may have one or more vectors attached directly or indirectly to their surfaces. Generally it will be preferred to attach a plurality (eg. 2 to 50) of vector moieties per particle. Particularly conveniently, besides the desired targeting vector, one will also attached flow decelerating vectors to the particles, ie. vectors which have an affinity for the capillary lumen or other organ surfaces which is sufficient to slow the passage of the contrast agent through the capillaries or the target organ but not sufficient on its own to immobilise the contrast agent. Such flow decelerating vectors (described for example in GB9700699.3) may moreover serve to anchor the contrast agent once it has bound to its target site.

The means by which vector to particle attachment is achieved will depend on the nature of the particle surface. For inorganic particles, the linkage to the particle may be for example by way of interaction between a metal binding group (eg. a phosphate, phosphonate or oligo or polyphosphate group) on the vector or on a linker attached to the vector. For organic (eg. polymeric) particles, vector attachment may be by way of direct covalent bonding between groups on the particle surface and reactive groups in the vector, eg. amide or ester bonding, or by covalent attachment of vector and particle to a linker. Linkers of the type discussed above in connection with chelated metal reporters may be used although in general the linkers will not be used to couple particles together.

For non-solid particles, eg. droplets (for example of water insoluble iodinated liquids as described in U.S. Pat. No. 5,318,767, U.S. Pat. No. 5,451,393, U.S. Pat. No. 5,352,459 and U.S. Pat. No. 5,569,448) and vesicles, the linker may conveniently contain hydrophobic "anchor" groups, for example saturated or unsaturated $C_{12-30}$ chains, which will penetrate the particle surface and bind vector to particle. Thus for phospholipid vesicles, the linker may serve to bind the vector covalently to a phospholipid compatible with the vesicle membrane. Examples of linker binding to vesicles and inorganic particles are described in GB9622368.0 and PCT/GB97/00067.

Besides the vectors, other groups may be bound to the particle surface, eg. stabilisers (to prevent aggregation) and biodistribution modifiers such as PEG. Such groups are discussed for example in PCT/GB97/00067, t WO96/09840, EP-A-284549 and U.S. Pat. No. 4,904,479.

Preferably the V—L—R agents of the invention will have the receptor targetting vectors coupled directly or indirectly to a reporter, eg. with covalently bound iodine radioisotopes, with metal chelates attached directly or via an organic linker group or coupled to a particulate reporter or linker-reporter, eg. a superparamagnetic crystals (optionally coated, eg. as in PCT/GB97/00067), or a vesicle, e.g. an iodinated contrast agent containing micelle or liposome.

Put briefly, for the imaging modalities of MRI, X-ray, light imaging, nuclear imaging, magnetotomography and electrical impedance tomography, the favoured reporters may be as follows:

MRI Superparamgnetic iron oxide particles, in general having a particle size smaller than about 80 nm. In particular iron oxides coated with various coating materials such as polyelectrolytes, PEG, starch and hyrolyzed starch are preferred. Paramagnetic metal substances including both chelates and particulate materials are also useful.

Light imaging Any light imaging reporter group. The focus should be on substances absorbing in the near infrared range.

Nuclear medicine Radioactive chelates comprising $^{99}$Tc or $^{111}$In as well as direct radiolabelled vectors having radiolabelled halogens substituents such as $^{123}$I, $^{125}$I, $^{131}$I, $^{75}$Br or $^{77}$Br Magnetotomography Superparmagnetic iron oxide particles as described above.

Electrical Polyionic species, e.g. polymers impedance with ionic groups in the repeat tomography units.

The agents of the invention may be administered to patients for imaging in amounts sufficient to yield the desired contrast with the particular imaging technique. Where the reporter is a metal, generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range of from 0.02 to 1.2 mmoles/kg bodyweight while for X-ray applications dosages of from 0.05 to 2.0 mmoles/kg are generally effective to achieve X-ray attenuation. Preferred dosages for most X-ray applications are from 0.1 to 1.2 mmoles of the lanthanide or heavy metal compound/kg bodyweight. Where the reporter is a radionuclide, dosages of 0.01 to 100 mCi, preferably 0.1 to 50 mCi will normally be sufficient per 70 kg bodyweight. Where the reporter is a superparamagnetic particle, the dosage will normally be 0.5 to 30 mg Fe/kg bodyweight.

The dosage of the compounds of the invention for therapeutic use will depend upon the condition being treated, but in general will be of the order of from 1 pmol/kg to 1 mmol/kg bodyweight.

The compounds of the present invention may be formulated with conventional pharmaceutical or veterinary aids, for example emulsifiers, fatty acid esters, gelling agents, stabilizers, antioxidants, osmolality adjusting agents, buffers, pH adjusting agents, etc., and may be in a form suitable for parenteral administration, for example injection or infusion or administration directly into the vasculature. Thus the compounds of the present invention may be in conventional pharmaceutical administration forms such as solutions, suspensions and dispersions in physiologically acceptable carrier media, for example water for injections.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Parenterally administrable forms, e.g. intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

The agents of formula I may be therapeutically effective in the treatment effective in the treatment of disease states as well as detectable in in vivo imaging. Thus for example the vector on the reporter moieites may have therapeutic efficacy, eg. by virtue of the radiotherapeutic effect of a radionuclide reporter, the efficacy in photodynamic therapy of a chromophore (or fluorophore) reporter or the chemotherapeutic effect of the vector moiety.

Use of the agents of formula I in the manufacture of therapeutic compositions and in methods of therapeutic or prophylactic treatment of the human or non-human animal body are thus considered to represent further aspects of the invention.

The present invention will now be further illustrated by way of the following non-limiting examples. Unless otherwise indicated, all percentages given are by weight.

EXAMPLE 1

Contrast Agent for MR Imaging of Angiogenesis
Compound 1

Lysine (0.1 g, 0.7 mmol) is added to a solution of $N^2$-[3S-hydroxy-4-(N-hydroxyamino)2R-isobutylsuccinyl]-L-(4-oxymethylcarboxy) phenylalanine-$N^1$-methylamide (prepared in accordance with WO94/02447, 0.3 g, 0.7 mmol) and DCC (N,N-dicyclohexylcarbodiimide) in dry DMF (N,N-dimethylformamide). The reaction mixture is stirred at ambient temperature and is followed by TLC.

The dispersion is left overnight at +4° C. The dispersion is filtered and the solvent rotary evaporated before the substance is purified by chromatography.

Compound 2

Diethylenetriaminepentaacetic acid dianhydride (17.9 g, 50 mmol) is dissolved in dry DMF and compound 1 (0.3 g, 0.5 mmol) dissolved in dry DMF is added. The reaction mixture is stirred at elevated temperature under nitrogen atmosphere. The reaction is followed by TLC. The solvent is rotary evaporated and the substance purified by chromatography.

Gd(III) Chelate of compound 2

To a solution of compound 2 (0.4 g, 0.4 mmol) in water is added gadolinium oxide $Gd_2O_3$ (0.1 g, 0.2 mmol) and the mixture is heated at 95° C. After filtration the solution is evaporated and dried in vacuo at 50° C.

EXAMPLE 2

Contrast Agent for MR Imaging of Angiogenesis

Compound 3

Lysine (0.1 g, 0.7 mmol) is added to a solution of N-(4-octylphenyl)-3-(2-carboxyethyl)-6,7-dihydro-5H-thiazolo[3,2-a]pyrimidine-2-carboxamide (prepared in accordance with EP-A-618208, 0.3 g, 0.7 mmol) and DCC (N,N'-dicyclohexylcarbodiimide) in dry DMF (N,N-dimethylformamide). The reaction mixture is stirred at ambient temperature and is followed by TLC. The dispersion is left overnight at +4° C. The dispersion is filtered and the solvent rotary evaporated before the substance is purified by chromatography.

Compound 4

Diethylenetriaminepentaacetic acid dianhydride (17.9 g, 50 mmol) is dissolved in dry DMF and compound 3 (0.3 g, 0.5 mmol) dissolved in dry DMF is added. The reaction mixture is stirred at elevated temperature under nitrogen atmosphere. The reaction is followed by TLC. The solvent is rotary evaporated and the substance purified by chromatography.

Gd(III) Chelate of compound 4

To a solution of compound 4 (0.4 g, 0.4 mmol) in water is added gadolinium oxide $Gd_2O_3$ (0.1 g, 0.2 mmol) and the mixture is heated at 95° C. After filtration the solution is evaporated and dried in vacuo at 50° C.

EXAMPLE 3

Contrast Agent for Nuclear Medicine for Detection of Angiogenesis $^{99m}$Tc Chelate of Compound 2

Compound 2 from Example 1 (1 mg) is dissolved in 0.1 N NaOH. $SnCl_2.2H_2O$ (100 μg) dissolved in 0.05 N HCl and a solution of 10–100 mCi $^{99m}$Tc in the form of sodium pertechnetate in saline is added. The pH of the solution is adjusted to pH 7–8 by addition of 0.5 M phosphate buffer (pH 5) after less than one minute. The reaction is followed by TLC and the substance is purified by chromatography.

EXAMPLE 4

Contrast Agent for Nuclear Medicine for Detection of Angiogenesis $^{99m}$Tc Chelate of Compound 4

Compound 4 from Example 2 (1 mg) is dissolved in 0.1 N NaOH. $SnCl_2.2H_2O$ (100 μg) dissolved in 0.05 N HCl and a solution of 10–100 mCi $^{99m}$Tc in the form of sodium pertechnetate in saline is added. The pH of the solution is adjusted to pH 7–8 by addition of 0.5 M phosphate buffer (pH 5) after less than one minute. The reaction is followed by TLC and the substance is purified by chromatography.

EXAMPLE 5

Contrast Agent for Nuclear Medicine for Detection of Angiogenesis

An aqueous solution of $^{131}I_2$ (2 equivalents) and sodium perchlorate (1 equivalent) is added to an aqueous solution of $N^2$-[3S-hydroxy-4-hydroxyamino) -2R-isobutylsuccinyl)-L-phenylalanine-$N^1$-methylamide (prepared in accordance with WO94/02446, 1 equivalent). The solvent is rotary evaporated and the substance is purified by chromatography.

EXAMPLE 6

Preparation of a DTPA Monoamide Gadolinium Complex Comprising a Vector for Targeting of VEGF Receptor for MR Detection of Angiogenesis

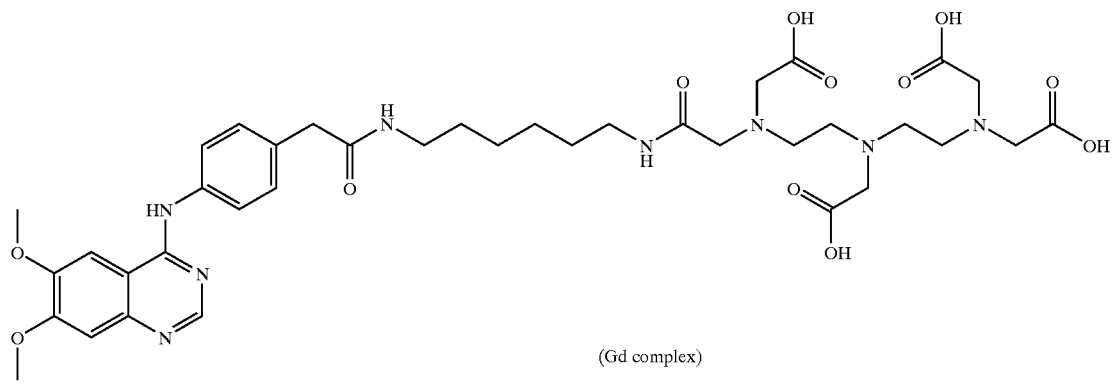

(Gd complex)

a) Synthesis of 6,7-Dimethoxy-3H-cuinazolin-4-one

A mixture of 2-amino-4,5-dimethoxybenzoic acid (9.9 mg, 0.050 mmol) and formamide (5 ml) was heated at 190° C. for 6 hours. The mixture was cooled to 80° C. and poured onto water (25 ml). Precipitated material was filtered off, washed with water and dried in vacuo. Yield 1.54 g (15%), brown powder. The structure was confirmed by $^1$H (500 MHz) and $^{13}$C NMR (125 MHz) analysis.

b) Synthesis of 4-Chloro-6.7-dimethoxyruinazoline

A suspension of compound from a) (1.03 g, 5.00 mmol) in phosphorousoxychloride (20 ml) was refluxed for 3 hours. The dark solution was concentrated and the residue was taken up in ethyl acetate. The organic phase was washed with saturated sodium bicarbonate solution and dried ($MgSO_4$). The solution was filtered through a short silica column and concentrated to give 392 mg (35%) of off-white material. $^1H$ NMR (300 MHz) and $^{13}C$ NMR (75 MHz) spectra were in accordance with the structure.

c) Synthesis of [4-(6.7-Dimethoxy-auinazolin-4-yvamino)-phenyllacetic Acid

A mixture of compound from b) (112 mg, 0.500 mmol) and 4-aminophenylacetic acid (76 mg, 0.50 mmol) in 2-propanol (8 ml) was refluxed for 3 hours. The reaction mixture was cooled and precipitated material was isolated, washed with 2-propanol and dried in vacuo. Yield 183 mg (97%), pale yellow solid material. The structure was verified by $^1H$ NMR (500 MHz) and $^{13}C$ NMR (125 MHz) analysis. Further characterisation was carried out using MALDI mass spectrometry (α-cyano-4-hydroxycinnamic acid matrix), giving m/z for [MH]$^+$ at 341, expected 340.

d) Synthesis of t-butyl (6-{2-[4-(6,7-Dimethoxy--quinazolin-4-ylamino)phenyl]acetylamino}hexyl) carbamate To a suspension of compound from c) (38 mg, 0.10 mmol) and N-Boc-1,6-diaminohexane hydrochloride (25 mg, 0.10 mmol) in DMF (2.0 ml) was added N,N-diisopropylethyl-amine (34 ml, 0.20 mmol). To the clear solution was added N-(3-dimethylaminopropyl)-N'-ethylcarbodiimid hydrochloride (19 mg, 0.10 mmo) and 1-hydroxybenzo-triazole (15 mg, 0.10 mmol). The reaction mixture was stirred at room temperature overnight and then poured onto 25 ml of water containing sodium carbonate (2.5 g) and sodium chloride (4.0 g). Organic material was extracted into chloroform and the organic phase was ashed with water and dried ($Na_2SO_4$). The solution was filtered and concentrated. The product was purified by column chromatography (silica, chloroform/methanol/acetic acid 85:10:5) and finally lyophilised from acetic acid. Yield 54 mg (90%), yellow-white solid material (acetate). The product was characterised by MALDI mass spectrometry (α-cyano-4-hydroxycinnamic acid matrix), giving m/z for [MH]$^+$ at 539 as expected.

Further characterisation was carried out using $^1H$ (500 MHz) and $^{13}C$ (125 MHz) NMR spectroscopy.

e) Synthesis of N-(6-aminohexyl)-[4-(6,7-dimethoxy-quinazolin-4-ylamino)phenyl]acetamide Hydrochloride Compound from d) (27 mg, 0.050 mmol) was dissolved in dioxane (3 ml) by gentle heating. To the solution was added 4 N HCl in dioxane (0.5 ml). The reaction mixture was stirred overnight and concentrated in vacuo to give a quantitative yield of the title compound. Characterisation was carried out using MALDI mass spectrometry (a-cyano-4-hydroxycinnamic acid matrix), giving m/z for [MH]$^+$ at 439 as expected. Further characterisation was carried out using analytical HPLC (column Vydac 218TP54, gradient 12–24% B over 20 min, A=water/0.1% TFA, B=acetonitrile/0.1% TFA, flow rate 1.0 ml/min) giving a single product peak with retention time 13.0 min detected at 340 nm. Characterisation was also carried out by means of NMR spectroscopy, giving $^1H$ (500 MHz) and $^{13}C$ (125 MHz) spectra in accordance with the structure.

f) Synthesis of a DTPA Monoamide Derivative for Gadolinium Chelation (Structure Shown Above)

N,N-Diisopropylethylamine (17 μl, 0.10 mmol) was added to a suspension of compound from e) (0.05 mmol) and DTPA-anhydride (179 mg, 0.500 mmol) in DMF (5 ml). The mixture was stirred at room temperature for 2 hours and concentrated in vacuo. HPLC analysis (column Vydac 218TP54, gradient 16–28% B over 20 minutes, A=water/0.1% TFA, B=acetonitrile/0.1% TFA, flow rate 1.0 ml/min) gave a product peak at 7.9 min shown by LC-MS (ESI) to correspond to the title compound (m/z for [MH]$^+$ at 813, expected 814). The product was purified by preparative HPLC (column Vydac 218TP1022, gradient 16–28% B over 60 min, A=water/0.1% TFA, B=acetonitrile/0.1% TFA, flow rate 10.0 ml/min, detection at 254 nm) giving a yield of 6.7 mg of purified material. Analytical HPLC analysis of purified material showed a shift in retention time to 5.6 min (analytical conditions as described above), shown by MALDI mass spectrometry to correspond to the iron complex, giving m/z at 870 for the complex and 816 for the free ligand.

g) Preparation of the Gadolinium Complex of Compound from f)

Compound from f) (0.1 mg) was dissolved in an aqueous solution of gadolinium trichloride (conc 2 mg/ml, 0.1 ml). The mixture was stirred overnight. Quantitative conversion to the gadolinium complex was verified by MALDI mass spectrometry (α-cyano-4-hydroxycinnamic acid matrix), giving m/z peaks at 970, 992 and 1014 for the gadolinium complex (gadolinium, gadolinium/sodium and gadolinium/disodium, respectively) and at 8:16/838 corresponding to the free ligand/sodium complex. No trace of the iron complex could be detected.

EXAMPLE 7

Preparation of a DTPA Bisamide Gadolinium Complex Comprising a Vector for Targeting of VEGF Receptor for MR Detection of Angiogenesis

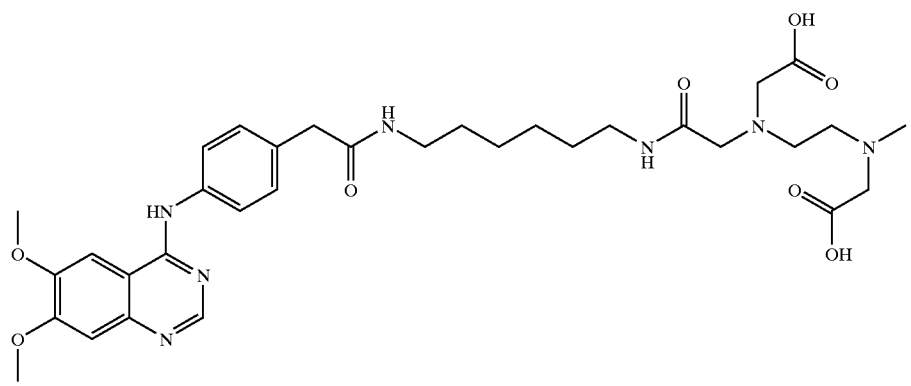

-continued

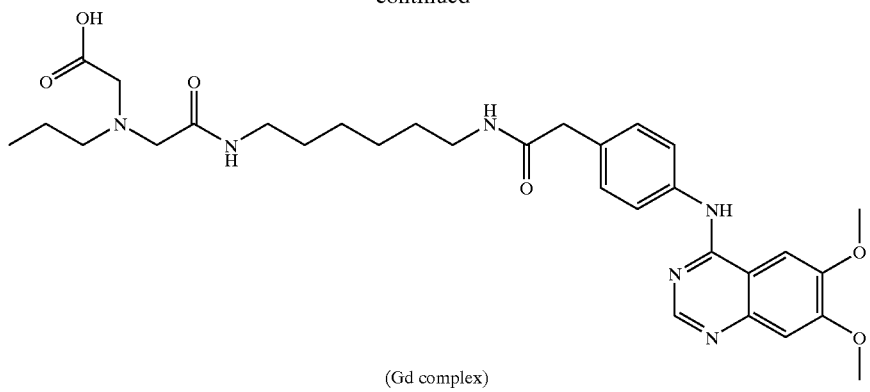

(Gd complex)

a) Synthesis of a DTPA Bisamide Derivative for Qadolinium Chelation (Structure Shown Above)

Analytical HPLC of the reaction mixture in Example 6f) gave also a peak at 16.8 min that was shown by LC-MS (EIS) analysis to correspond to the DTPA bisamide shown above, giving m/z at 1233 for [MH]⁺ as expected and 616.6 as expected for [MH$_2$]$^{2+}$. The product was purified by preparative HPLC (conditions as described in Example 6f)) to give 14 mg of pure material after lyophilisation. Analytical HPLC analysis of the purified material showed a shift in retention time from 16.8 min (in the crude mixture) to 11.1 min due to formation of the iron complex during purification, as verified by MALDI mass spectrometry (α-cyano-4-hydroxy-cinnamic acid matrix) giving m/z at 1291 for the iron complex and 1237 for the free ligand.

b) Preparation of the Gadolinium Complex of Compound from a)

The compound from a) was treated with an of gadolinium trichloride as described in Example 6g). After 2 hours reaction time MALDI mass spectrometry showed conversion to the gadolinium complex, giving m/z at 1391 for the gadolinium complex and 1235 for the free ligand.

EXAMPLE 8

Carboxymethyl-[2-(carboxymethyl-{2-[carboxymethyl-({2-[3-({3-oxo-2-[2-(pyridin-2-ylamino)-ethyl]-2,3-dihydro-1H-isoindole-5-carbonyl}-amino)-propionylamino]-ethylcarbamoyl}-methyl)-amino]-ethyl}-amino)-ethyl]-amino}-acetic Acid (12)

a) 4-Methyl-isophthalic Acid (2)

To THF (130 ml) solution of 3-bromo-4-methyl-benzoic acid (5.0 g, 23.25 mmol) under nitrogen and cooled to −78° C. (dryice/methanol) was added MeMgBr in ether (3.0 M, 8.5 ml, 25.57 mmol) at such a rate that the temperature did not exceed −75° C. The temperature was then allowed to rise to −60° C. and after gas evolution had ceased, the solution was cooled again to −78° C. BuLi in hexane (1.6 M, 29.06 ml, 46.50 mmol) was then added dropwise such that the temperature did not rise above −75° C. The mixture was then stirred at this temperature for 15 minutes before crushed dryice (4.4 g, 100 mmol) was added. The precipitate was vigorously stirred as the temperature was allowed to freely rise to ambient temperature. The mixture was made acidic using 6 N HCl and the solid material collected filteration, washed with diethyl ether and dried. Recrystallisation from water afforded off-white pure compound (81%) m.p. 296–298° C. (sublimed). NMR conforms to expected structure.

b) 4-Methyl-isophthalic Methyl Ester (4)

A mixture of compound (2) (2.83 g, 15.71 mmol), thionyl chloride (50 ml) and DMF (3 drops) was heated at reflux for 2 hours. After cooling to room temperature, excess thionyl chloride was removed under reduced pressure (rotary evaporator). The dark oil which was obtained was dissolved in carbon tetrachloride (30 ml), treated with pyridine (1 ml, 12.43 mmol) and methanol (20 ml) and stirred at ambient temperature for 2 hours. The solvents were evaporated and the residue purified by flash chromatography: silica, hexane/EtOAc (9:1).

c) 4-Bromoethyl-isophthalic Acid Dimethylester (5)

A mixture of (4) (0.96 g, 4.61 mmol), dibenzoylperoxide (56 mg, 0.23 mmol) and N-bromosuccinimide (NBS) (0.82 g, 4.61 mmol) in carbon tetrachloride (20 ml) was heated at reflux for 20 hours. After cooling to room temperature and filteration the solvent was evaporated to-give a yellow oil. Flash chromatograph: silica, hexane/EtOAc (7:3) afforded the pure compound.

d) 3-oxo-[2-(pyridin-2-ylamino)-ethyl]-2,3-dihydro-1H-isoindole-5-carboxylic Acid Methyl Ester (6)

A solution of (5) (511 mg, 1.78 mmol) in toluene (10 ml) was treated with Et$_3$N (744 μl, 5.33 mmol) and N1-pyridin-2-yl-ethane-1,2-diamine (244 mg, 1.78 mmol) [prepared by treatment of 2-bromopyridine with excess ethylene diamine and pyridine] and the mixture refluxed for 6 hours. After

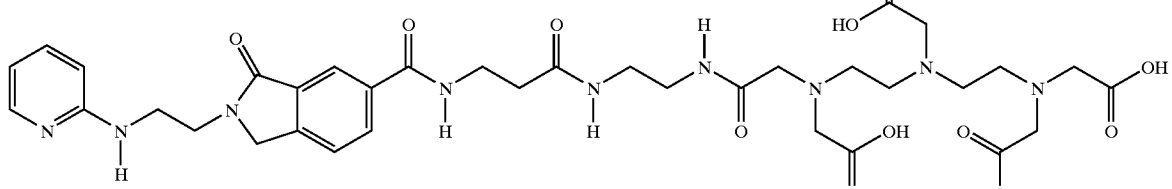

cooling to room temperature and evaporation of the solvent, the residue was purified by flash chromatography: silica, CH$_2$Cl$_2$/acetone (3:2).

e) 3-oxo-2-[2-pyridin-2-ylamino)-ethyl]2.3-dihydro-1H-isoindole-5-carboxylic Acid (7)

A methanol solutin (6 ml) of (6) (301 mg, 0.97 mmol) and 1 N NaOH (3 ml) was stirred at ambient temperature for 24 hours. The solution was made acidic using 1 M NaHSO$_4$ solution and the precipitated product was collected by filtteration washed thoroughly with water and dried over P$_2$O$_5$/bluegel for 24 hours.

f) 3-({3-oxo-2-[2-(Dyridin-2-ylamino)-ethyl]2,3-dihydro-1H-isoindole-5-carbonyl}-amino)-propionic Acid tert-butyl Ester (8)

A solution of (7) (166 mg, 0.56 mmol), N-methyl morfolin (185 μl, 1.68 mmol), BOP (322 mg, 0.73 mmol) and H-β-ala-OtBu (152 mg, 0.84 mmol) in DMF (5 ml) was stirred at ambient temperature for 20 hours. The mixture was diluted with ethyl acetate (10 ml) and then washed once each with H$_2$O, NaHCO$_3$, 10% KHSO$_4$ and brine (5 ml), dried (MgSO$_4$) and concentrated. Flash chromatography (silica, EtOAc) gave the ester (8) as a white solid.

g) 3-({3-oxo-2-[2-(pyridin-2-ylamino)-ethyl]2,3-dihydro-1H-isoindole-5-carbonyl}-amino)-propionic Acid (9)

A solution of the ester (8) (252 mg, 0.60 mmol), TFA (4 ml) and CH$_2$Cl$_2$ (8 ml) was stirred at ambient temperature for 3 hours. The mixture was evaporated to dryness and the residue purified by flash chromatography (silica, EtOH/ NH$_4$OH 19:1) to provide (9) as off-white foam. NMR conforms to structure.

and concentrated. Flash chromatography (silica, 1:1 CH$_2$Cl$_2$/acetone). MALDI-MS; 510.59.

i) 3-Oxo-2-[2-(pyridin-2-vlamino)-ethyl]-2,3-dihydro-1H-isoindole-5-carbdxylic Acid [2-(2-amino-ethylcarbamoyl)-ethyl]-amide (11)

A CH$_2$Cl$_2$ solution (3 ml) of (10) (20 mg, 0.039 mmol) and TFA (2 ml) was stirred under ambient conditions for 4 hours. The reaction mixture was concentrated and the residue purified by flash chromatography (silica, 19:1, CH$_2$Cl$_2$/ acetone) to provide (4) as a white solid. MALDI-MS; 410.48.

j) Carboxymethyl-[2-(carboxymethyl-{2-[carboxymethyl-({2-[3-({3-oxo-2-[2-(pyridin-2-ylamino)-ethyl]-2,3-dihydro-1H-isoindole-5-carbonyl}-amino)-propionylamino]-ethylcarbamoyl}-methyl)-amiino]-ethyl}-amino)-ethyl]-amino}-acetic Acid (12)

A solution of (11) (15 mg, 0.36 mmol), N,N-diisopropylamine (17 μl, 0.10 mmol) and DTPA-anhydride (129 mg, 0.36. mmol) in DMF (2 ml) was stirred at ambient temperature for 3 hours and concentrated in vacuo. The residue was purified by preparative HPLC (acetonirile/0.1% TFA in water).

EXAMPLE 9

Preparation of a DTPA Monoamide Gadblinium Complex Comprising a Vector for Targeting of bFGF Receptor for MR Detection of Angiogenesis

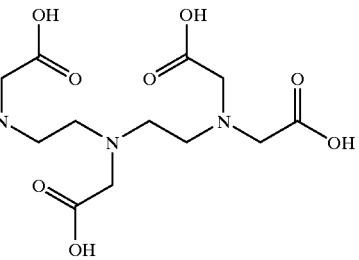

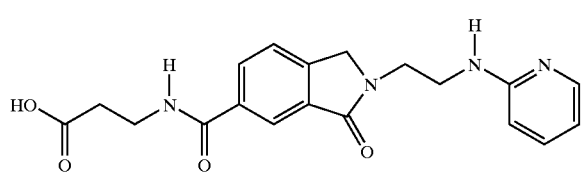

h) (2-[3-({3-Oxo-2-[2-(pyridin-2-ylamino)-ethyl]-2.3-dihydro-1H-isoindole-5-carbonyl-amino)-oropionylaminol-ethyl}-carbamic acid tert-butyl Ester (10)

To absolution of the acid (9) (20 mg, 0.054 mmbl) in DMF (2 ml) was added N-methyl morfolin (NMM)-(16.40 mg, 0.162 mmol), BOP (castro's reagent) 31.05 mg, 0.070 mmol) and the BOC-protected diamine (13 mg, 0.081 mmol) and the mixture was stirred at ambient temperature for 20 hours. After dilution with EtOAc (5 ml), the solution was washed once each with H$_2$O, sat. NaHCO$_3$, 10% KHSO$_4$ and brine. The organic phase was dried (MgSO$_4$)

a) Synthesis of: {3-[2-(4-Chloro-benzyloy)-2-(2,4-dichloro-phenyl)-ethyl]-3H-imidazol-1-yl}-acetic Acid tert-butyl Ester 1-[2-(4-chloro-benzyloxy)-2-(2,4-dichloro-phenyl)-ethyl]-1H-imidazole (1 g, 2.25 mmol) and tert-butyl bromoacetate (1 ml, 6.8 mmol) were dissolved in 15 ml acetonitrile and heated to reflux overnight. TLC showed full conversion of the starting material. The solvent was cooled, evaporated in vacuo, and the residual oil was dissolved in chloroform and triturated with ether. The product was identified by Maldi mass spectrometry, and used in the next step without further purification.

b) Synthesis of: {3-[2-(4-chloro-benzvloxy)-2-(2,4-dichloro-phenyl)-ethyl]-3H-imidazol-1-yl}-acetic Acid The compound from a) (500 mg, 1 mmol) was dissolved in 2 ml dichloromethane and cooled in an icebath. 2 ml trifluoroacetic acid was added, the icebath was removed and the reaction-mixture was stirred for 1 hour. TLC showed full conversion of the starting material. The solvent was removed in vacuo, and the product used in the next step without further purification.

c) Synthesis of: [6-(2-{3-[2-(4-chloro-benzyloxy)-2-(2,4-dichloro-phenyl)-ethyl]-3H-imidazol-1-yl}-acetylamino)-hexyl]-carbamic Acid tert-butyl Ester The product from b) was converted to c) by the procedure described for Example 6 d), and the product was purified by flash chromatography.

d) Synthesis of: N-(6-Amino-hexyl)-2-{3-[2-(4-chloro-benzyloxvy)-2-(2,4-dichloro-phenyl)-ethyl]-3H-imidazol-1-yl}-acetamide The product from c) was converted to d) by the procedure described for Example 6 e). The product was used without further purification.

e) Synthesis of: ((2-{[2-(bis-Carboxymethyl-amino)-ethyll-carboxymethyl-amino}-ethyl)-{[6-(2-{3-[2-(4-chloro-benzyloxy)-2-(2,4-dichloro-phenyl-)-ethyl]-3H-imidazol-1-yl}-acetylamino)-hexylcarbamoyl]-methyl}-amino)-acetic Acid The product from d) was converted to e) by the procedure described for Example 6 f). Purification was performed by preparative HPLC as described in Example 6 f).

f) Preparation of the Gadolinium Complex of Compound e) was Performed by the Procedure Described in Example 6 g).

What is claimed is:

1. A composition of matter of formula I $$V—L—R \qquad (I)$$

where V is a vector moiety having affinity for an angiogenesis-related endothelial cell receptor, L is a linker moiety or a bond and R is a detectable moiety, characterised in that V is peptidic and R is a macromolecular or particulate species providing a multiplicity of labels detectable in in vivo imaging.

2. A composition of matter of formula I $$V—L—R \qquad (I)$$

where V is a vector moiety having affinity for an angiogenesis-related endothelial cell receptor and is selected from the group consisting of a vector for integrin receptor, a vector for fibronectin receptor, a vector for the VEGF receptor, and a vector for the urokinase plasminogen activator receptor (UPAR),
L is a linker moiety or a bond and R is a macromolecular or particulate species providing a multiplicity of labels detectable in in vivo imaging.

3. A composition of matter as claimed in claim 1 wherein V is a peptide or peptoid moiety.

4. A composition of matter as claimed in claim 2 wherein V is a vector for integrin receptor.

5. A composition of matter as claimed in claim 2 wherein V is a vector for fibronectin receptor.

6. A composition of matter as claimed in claim 2 wherein V is a vector for the VEGF receptor.

7. A composition of matter as claimed in claim 2 wherein V is a vector for the urokinase plasminogen activator receptor (UPAR).

8. A composition of matter of formula I $$V—L—R \qquad (I)$$

where L is a linker moiety or a bond, R is a macromolecular or particulate species providing a multiplicity of labels detectable in in vivo imaging, and wherein V is selected from the group of vector moieties consisting of:
$N^2$-[3S-hydroxy-4-(N-hydroxyamino)2R-isobutylsuccinyl]-L-(4-oxymethylcarboxy)phenylalanine-$N^1$-methylamide,
N-(4-octylphenyl)-3-(2-carboxyethyl)-6,7-dihydro-5H-thiazolo[3,2-a] pyrimidine-2-carboxamide, N²-[3S-hydroxy-4-hydroxyamino)-2R-isobutylsuccinyl]-L-phenylaianine-N¹-methylamide, N-(6-aminohexyl)-[4-(6,7-dimethoxy-quinazolin-4-ylamino)phenyl]acetamide hydrochloride, 3-Oxo-2-[2-(pyridin-2-ylamino)-ethyl]-2,3-dihydro-1H-isoindole-5-carboxylic acid [2-(2-amino-ethylcarbamoyl)-ethyl]-amide, and N-(6-amino-hexyl)-2-{3-[2-(4-chloro-benzyloxy)-2-(2,4-dichloro-phenyl)-ethyl]-3H-imidazol-1-yl}-acetamide.

9. A composition of matter of formula I

 (I)

which is-selected from the following residues:

Gd (III), $^{99m}$Tc or $^{131}$I$_2$ chelates of the vector moieties selected from the group consisting of:

N²-[3S-hydroxy-4-(N-hydroxyamino)2R-isobutylsuccinyl-L-(4-oxymethylcarboxy)phenylalanine-N¹-methylamide, N-(4-octylphenyl)3-(2-carboxyethyl)-6,7-dihydro-5H-thiazolo[3,2-a]pyrimidine-2-carboxamide, N²-[3S-hydroxy-4-hydroxyamino)-2R-isobutylsuccinyl]-L-phenylalanine-N¹-methylamide, N-(6-aminohexyl)-[4-(6,7-dimethoxy-quinazolin-4-ylamino)phenyl]acetamide hydrochloride, 3-Oxo-2-[2-(pyridin-2-ylamino)-ethyl]-2,3-dihydro-1H-isoindole-5-carboxylic acid [2-(2-amino-ethylcarbamoyl)-ethyl]-amide, and N-(6-amino-hexyl)2-{3-[2-(4-chloro-benzyloxyy2-(2,4-dichloro-phenyl)-ethyl]-3H-imidazol-1-yl}-acetamide;

and having a DTPA chelating group.

10. A composition of matter as claimed in claim 1 wherein R is a radionuclide.

11. A composition of matter as claimed in claim 1 wherein R is an iodine or metal radionuclide.

12. A pharmaceutical composition comprising a composition of matter of formula I as defined in claim 1 together with at least one pharmaceutically acceptable carder or excipient.

13. A method of generating an image of an animate human or non-human animal subject involving administering a contrast agent to said subject and generating an image of at least a part of said subject to which said contrast agent has distributed, characterised in that as said contrast agent is used a composition of matter of formula I

 (I)

where V is a vector moiety having affinity for an angiogenesis-related endothelial cell receptor, L is a linker moiety or a bond and R is a detectable moiety, characterised in that V is peptidic and R is a macromolecular or particulate species providing a multiplicity of labels detectable in in vivo imaging.

14. A method of monitoring the effect of treatment of a human or non-human animal subject with a drug to combat or provoke effects associated with angiogenesis, said method involving administering to said subject a composition of matter of formula I

 (I)

where V is a vector moiety having affinity for an angiogenesis-related endothelial cell receptor, L is a linker moiety or a bond and R is a detectable moiety, characterised in that V is peptidic and R is a macromolecular or particulate species providing a multiplicity of labels detectable in in vivo imaging, and detecting the uptake of said agent by angiogenesis related endothelial cell receptors.

15. A method as claimed in claim 14 wherein said administration and detection are effected before, during and after treatment with said drug.

16. A process for the preparation of a composition of a matter of formula I

 (I)

where V is a vector moiety having binding affinity for an angiogenesis-related endothelial cell receptor, L is a linker moiety or a bond and R is a moiety, characterised in that V is peptidic and R is a macromolecular or particulate species providing a multiplicity of labels detectable in in vivo imaging, said process comprising conjugating moiety V with moiety R via the linker or bond L.

17. A composition of matter as claimed in claim 2 wherein R is a radionuclide.

18. A composition of matter as claimed in claim 8 wherein R is a radionuclide.

19. A composition of matter as claimed in claim 2 wherein R is an iodine or metal radionuclide.

20. A composition of matter as claimed in claim 8 wherein R is an iodine or metal radionuclide.

21. A pharmaceutical composition comprising a composition of matter of formula I as defined in claim 2 together with at least one pharmaceutically acceptable carrier or excipient.

22. A pharmaceutical composition comprising a composition of matter of formula I as defined in claim 8 together with at least one pharmaceutically acceptable carrier or excipient.

23. A pharmaceutical composition comprising a composition of matter of formula I as defined in claim 9 together with at least one pharmaceutically acceptable carrier or excipient.

* * * * *